(12) United States Patent
Hutchison et al.

(10) Patent No.: US 8,212,225 B2
(45) Date of Patent: Jul. 3, 2012

(54) TEM GRIDS FOR DETERMINATION OF STRUCTURE-PROPERTY RELATIONSHIPS IN NANOTECHNOLOGY

(75) Inventors: James E. Hutchison, Eugene, OR (US); Gregory J. Kearns, Foster City, CA (US)

(73) Assignee: State of Oregon acting by and through the State Board of Higher Education on behalf of the University of Oregon, Eugene, OR (US)

( * ) Notice: Subject to any disclaimer, the term of this patent is extended or adjusted under 35 U.S.C. 154(b) by 172 days.

(21) Appl. No.: 12/600,764

(22) PCT Filed: May 19, 2008

(86) PCT No.: PCT/US2008/064152
§ 371 (c)(1),
(2), (4) Date: Nov. 18, 2009

(87) PCT Pub. No.: WO2009/035727
PCT Pub. Date: Mar. 19, 2009

(65) Prior Publication Data
US 2010/0155620 A1 Jun. 24, 2010

Related U.S. Application Data

(63) Continuation-in-part of application No. PCT/US2006/019971, filed on May 23, 2006, and a continuation-in-part of application No. PCT/US2006/018716, filed on May 12, 2006.

(60) Provisional application No. 60/930,710, filed on May 18, 2007, provisional application No. 60/683,916, filed on May 23, 2005, provisional application No. 60/680,919, filed on May 13, 2005.

(51) Int. Cl.
*H01J 37/20* (2006.01)
*B32B 3/10* (2006.01)
*C23F 1/00* (2006.01)

(52) U.S. Cl. ............... 250/440.11; 250/311; 428/138; 430/311; 430/313; 427/162; 216/24; 977/954

(58) Field of Classification Search ............ 250/440.11, 250/311; 428/138; 430/311, 313; 427/162; 216/24; 977/954
See application file for complete search history.

(56) References Cited

U.S. PATENT DOCUMENTS
3,815,094 A 6/1974 Smith
(Continued)

FOREIGN PATENT DOCUMENTS
WO PCT/US2006/018716 5/2006
(Continued)

OTHER PUBLICATIONS
U.S. Appl. No. 60/680,919, filed May 13, 2005, Hutchison et al.
(Continued)

*Primary Examiner* — Nikita Wells
(74) *Attorney, Agent, or Firm* — Klarquist Sparkman, LLP

(57) ABSTRACT

Silicon grids with electron-transparent $SiO_2$ windows for use as substrates for high-resolution transmission electron microscopy of chemically-modified $SiO_2$ surfaces are fabricated by forming an oxide layer on a silicon substrate. An aperture is defined in the silicon substrate by etching the substrate to the oxide layer. A single substrate can include a plurality of apertures that are in respective frame regions that are defined by one or more channels in the substrate. Structural or chemical functionalizations can be provided, and surface interactions observed via TEM.

31 Claims, 12 Drawing Sheets

U.S. PATENT DOCUMENTS

| | | | |
|---|---|---|---|
| 5,409,777 | A | 4/1995 | Kennedy et al. |
| 5,612,588 | A | 3/1997 | Wakalopulos |
| 6,002,202 | A | 12/1999 | Meyer et al. |
| 6,013,534 | A | 1/2000 | Mountain |
| 6,803,570 | B1 | 10/2004 | Bryson, III et al. |
| 7,192,865 | B1 | 3/2007 | Ohtani et al. |
| 2004/0175631 | A1 | 9/2004 | Crocker et al. |
| 2004/0213910 | A1 | 10/2004 | Cai et al. |
| 2004/0265754 | A1 | 12/2004 | Barclay et al. |
| 2005/0058416 | A1 | 3/2005 | Hoon et al. |
| 2006/0243379 | A1 | 11/2006 | Livesay et al. |
| 2008/0280099 | A1* | 11/2008 | Hutchison et al. ............ 428/138 |
| 2009/0104435 | A1* | 4/2009 | Hutchison et al. ............ 428/328 |

FOREIGN PATENT DOCUMENTS

| | | |
|---|---|---|
| WO | PCT/US2006/019971 | 5/2006 |
| WO | WO 2006/127736 | 11/2006 |
| WO | PCT/US2008/064152 | 5/2008 |

OTHER PUBLICATIONS

U.S. Appl. No. 60/683,916, filed May 23, 2005, Hutchison et al.

U.S. Appl. No. 60/930,710, filed May 18, 2007, Hutchison et al.

International Search Report and Written Opinion for PCT/US2008/064152, dated Feb. 20, 2009, 8 pages.

International Search Report and Written Opinion for PCT/US2006/019971, dated Jul. 3, 2008, 6 pages.

International Preliminary Report on Patentability and Written Opinion for PCT/US2006/019971, dated May 12, 2009, 4 pages.

Bensimon et al., "Alignment and Sensitive Detection of DNA by a Moving Interface," Science, 265:2096-2098 (1994).

Grabar et al., "Nanoscale Characterization of Gold Colloid Monolayers: A Comparison of Four Techniques," Anal. Chem., 69:471-477 (1997).

Grant et al., "Transmission electron microscopy 'windows' for nanofabricated structures," Nanotechnology, 15:1175-1181 (2004).

Hidenobu et al., "Highly Ordered Assemblies of Au Nanoparticles Organized on DNA," Nano Lett., 3:1391-1394 (2003).

Ito et al., "Modification of Silicon Nitride Tips with Trichlorosilane Self-Assembled Monolayers (SAMs) for Chemical Force Microscopy," Langmuir, 13:4323-4332 (1997).

Kennedy et al, "Oxidation of silicon nitride films in an oxygen plasma," J. Appl. Phys., 85:3319-3326 (1999).

Michalet et al., "Dynamic Molecular Combing: Stretching the Whole Human Genome for High-Resolution Studies," Science, 277:1518-1523 (1997).

Warner et al, "Linear assemblies of nanoparticles electrostatically organized on DNA scaffolds," Nat. Mater., 2:272-277 (2003).

Warner et al., "Small, Water-Soluble, Ligand-Stabilized Gold Nanoparticles Synthesized by Interfacial Ligand Exchange Reactions," Chem. Mater., 12:3316 (2000).

Woehrle et al., "Molecular-Level Control of Feature Separation in One-Dimensional Nanostructure Assemblies Formed by Biomolecular Nanolithography," Langmuir, 127:2172-2183 (2005).

Office action from related U.S. Appl. No. 11/921,056, mailed Dec. 5, 2011.

\* cited by examiner

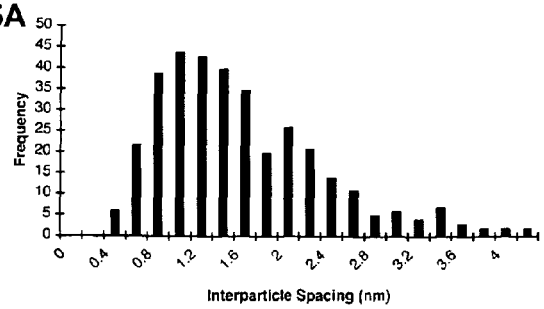
FIG. 5A Normally Prepared Au-TMAT
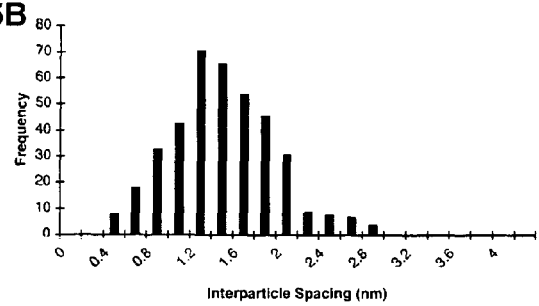
FIG. 5B Ultrapure Au-TMAT
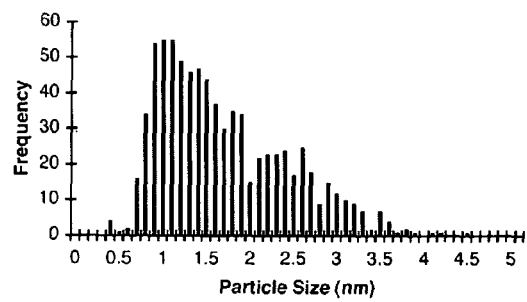
FIG. 6A
Au-TMAT
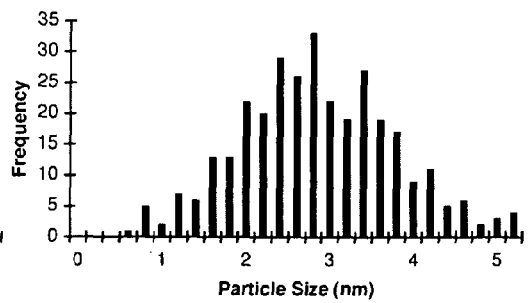
FIG. 6C
Au-TMAT on DNA
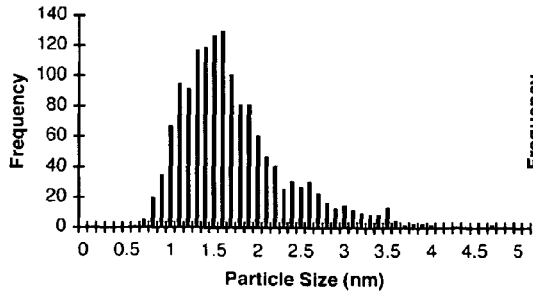
FIG. 6B
Ultrapure Au-TMAT
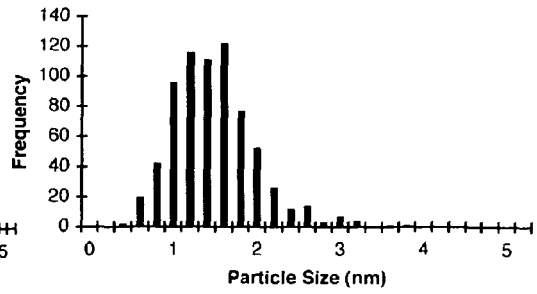
FIG. 6D
Ultrapure Au-TMAT on DNA

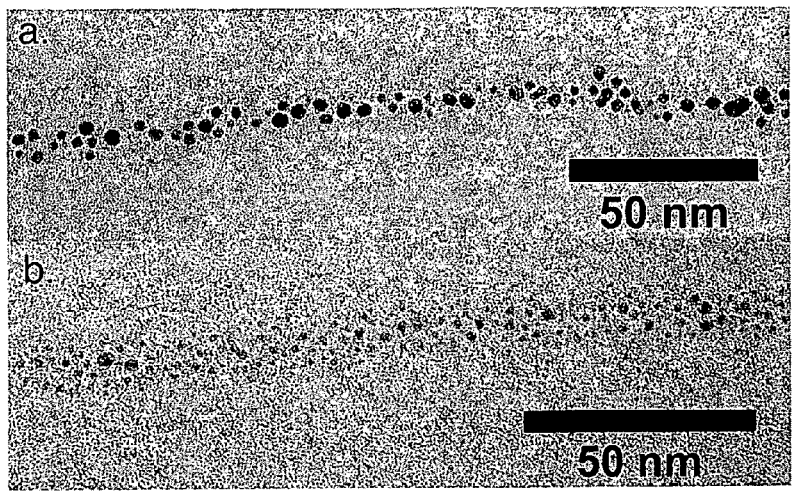
FIG. 7A
FIG. 7B
FIG. 8A
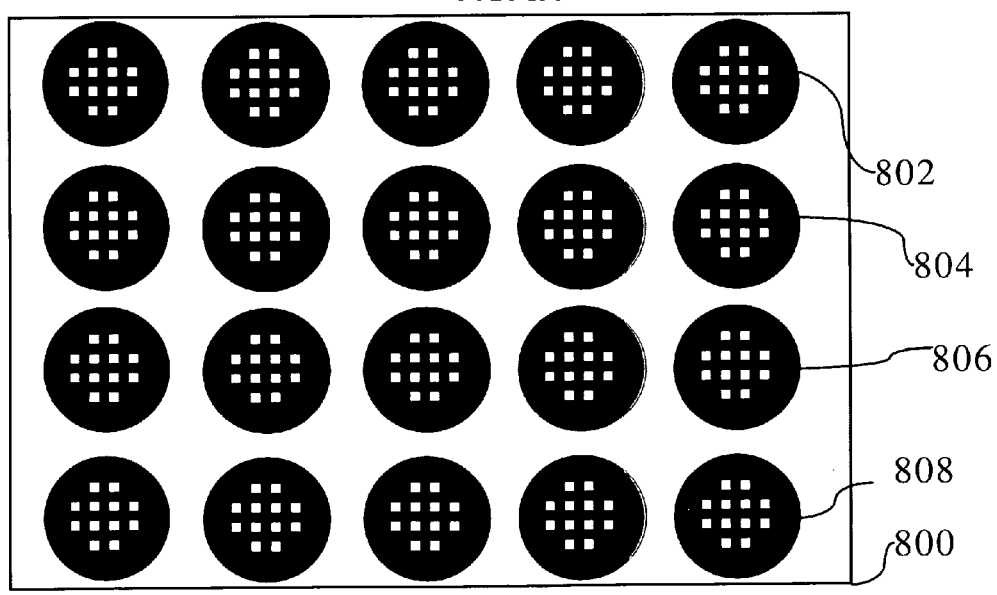
FIG. 8B
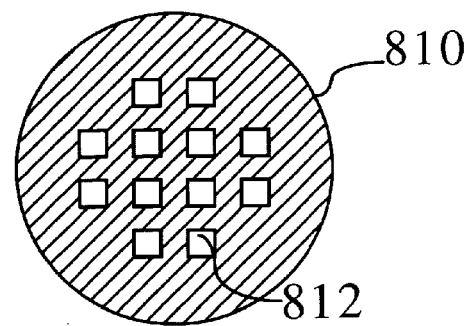

|← 3 mm →| d)

|← 10-30 µm →|

TEM GRIDS FOR DETERMINATION OF STRUCTURE-PROPERTY RELATIONSHIPS IN NANOTECHNOLOGY

CROSS-REFERENCE TO RELATED APPLICATIONS

This is the U.S. National Stage of International Application No. PCT/US2008/064152, filed May 19, 2008, which was published in English under PCT Article 21(2), which in turn claims the benefit of U.S. Provisional Application 60/930,710, filed May 18, 2007, and is a continuation-in-part of PCT Patent Application PCT/US2006/019971, filed May 23, 2006, that claims the benefit of U.S. Provisional Patent Application 60/683,916, filed May 23, 2005, and is a continuation-in-part of PCT Patent Application PCT/US2006/018716, filed May 12, 2006, that claims the benefit of U.S. Provisional Patent Application 60/680,919, filed May 13, 2005, all of which are incorporated herein by reference.

ACKNOWLEDGMENT OF GOVERNMENT SUPPORT

This invention was made with Government support under Contract FA8650-05-1-5041 awarded by the Air Force Laboratory. The Government has certain rights in the invention.

TECHNICAL FIELD

The disclosure pertains to substrates and patterned substrates for transmission electron microscopy.

BACKGROUND

An important challenge in nanoscience is the characterization and analysis of structures that are assembled on technologically relevant substrates. A number of scanning probe and electron beam-based microscopies have been employed, each possessing unique advantages, complexities and substrate requirements. Imaging performance is typically enhanced through the use of specialized substrates. Unfortunately, such substrates are often chemically dissimilar to the substrates used in devices or during assembly reactions. For example, a carbon-coated TEM grid has different surface chemistry than a semiconductor wafer.

The most commonly used methods for analyzing nanostructures on chemically functionalized surfaces are atomic force microscopy (AFM) and scanning electron microscopy (SEM) because these techniques are compatible with a wide range of substrates including $SiO_2$. In a direct comparison of AFM, SEM, scanning near-field optical microscopy (SNOM) and transmission electron microscopy (TEM), Grabar et al. demonstrated that TEM is a preferred method for quantifying the size, shape, and spacing of nanoparticles in nanoparticle arrays due to high lateral resolution and straightforward data analysis. Grabar et al., *Anal. Chem.* 1997, 69, 471-477. The primary limitation of using TEM to analyze nanostructures is that the relevant substrate material may not be available as a support film on commercially available grids. In order to obtain images of samples on relevant substrates, time-intensive, destructive sample preparation techniques such as mechanical polishing or ion milling must be employed in order to obtain electron transparency.

Commercially available silicon monoxide ($SiO_x$) TEM grids are often used as approximants for $SiO_2$ surfaces. These substrates generally consist of a metal grid coated with a polymer support that is coated with a substrate material such as SiO or carbon. Unfortunately, these substrates are rough, lack rigidity, and the SAX surfaces have an ambiguous chemical structure that is a mixture of SiO and $SiO_2$. Therefore, such surfaces do not have the same chemical reactivity as native or thermally grown $SiO_2$ on silicon. Due to the reactivity of the polymer coated metal grid that supports such SiO films, these grids cannot withstand even the mildest environments that are used for cleaning and processing $SiO_2$/Si. UV/ozone cleaning destroys the polymer support, as do RCA SC-1, piranha solution, and oxygen plasma, while RCA SC-2 or other acidic environments will dissolve most metal substrates. In addition, the chemical environments used to functionalize $SiO_2$, such as self-assembled monolayer chemistry, often involve acidic environments and organic solvents. The ideal TEM grid for imaging $SiO_2$ surfaces must be electron transparent, smooth, rigid, and robust to chemical processing.

Recently, it has been shown that the surfaces of silicon nitride TEM grids can be oxidized to $SiO_2$ by $O_2$ plasma treatment, but the chemical nature and reactivity of such surfaces has not been determined. See Grant et al., *Nanotechnology* 2004, 15, 1175. Because thermal oxides react differently to surface treatments than native oxides due to the nature of the surface hydroxyl groups, surfaces with a stoichiometry of $SiO_2$ are not necessarily equivalent. Thus it cannot be assumed that the images obtained from an oxidized silicon nitride TEM grid represent the surface of a similarly treated glass slide or silicon chip.

TEM grids with electron-transparent $Si_3N_4$ windows are commercially available. While Grant et al. report that grids of this type can be oxidized in an oxygen plasma to produce an $SiO_2$ surface, analytical data and the chemical reactivity of these surfaces have not been reported. Grant et al., "Transmission electron microscopy 'windows' for nanofabricated structures," *Nanotechnology*, 2004, 15, 1175-1181. Kennedy et al. report that the chemical composition of oxidized silicon nitride surfaces depends noticeably on the method of oxidation, ranging from an oxynitride composition at lower levels of oxidation toward a "silicon oxide rich" layer after more extensive oxidation. Kennedy et al, "Oxidation of silicon nitride films in an oxygen plasma," *J. Appl. Phys.*, 1999, 85, 3319-3326. Ito et al. have reported that the reactivity of the "native oxide" on silicon nitride depends on the method of sample preparation. Ito et al., "Modification of Silicon Nitride Tips with Trichlorosilane Self-Assembled Monolayers (SAMs) for Chemical Force Microscopy," *Langmuir,* 1997, 13, 4323-4332. Given the marked dependence of the surface reactivity of silicon dioxide and oxidized silicon nitride on the method of preparation (e.g. native oxide and thermal oxide exhibit different reactivity due, in part, to the differences in surface hydroxyl concentration), it remains to be seen whether oxidized silicon nitride surfaces will serve as suitable approximants for a thermal silicon dioxide surface. From the data published for the oxidized silicon nitride grids, it appears unlikely that these grids will exhibit the surface reactivity found for thermal silicon dioxide.

To scale electronic devices down to nanometer dimensions, fundamentally distinct new technologies are needed to provide smaller features that can confer heretofore unattainable electron flow control. The ultimate limit is a system in which the transfer of a single charge quantum corresponds to information transfer or some type of logic operation. Such single-electron systems are presently the focus of intense research activity. See, for example, *Single Charge Tunneling, Coulomb Blockade Phenomena in Nanostructure*, edited by H. Grabert and M. H. Devoret, NATO ASI Series B: Physics Vol. 294 (1992). These systems have potential application to nanoelectronic circuits that have integration densities far exceeding those of present day semiconductor technology. See, *Quantum Transport in Ultrasmall Devices*, edited by D. K. Ferry, H. L. Grubin, C. Jacoboni, and A. Jauho, NATO ASI Series B: Physics Vol. 342 (1995).

Single-electron transistors based on the concept of Coulomb blockade are one proposed technology for realizing ultra-dense circuits. Coulomb blockade is the suppression of single-electron tunneling into metallic or semiconductor islands. In order to achieve Coulomb blockade, the charging energy of an island must greatly exceed the thermal energy. To reduce quantum fluctuations the tunneling resistance to the island should be greater than the resistance quantum $h/e^2$. Coulomb blockade itself may be the basis of conventional logic elements, such as inverters. Equally promising is the use of the Coulomb blockade effect to pump charges one-by-one through a chain of dots to realize a frequency-controlled current source in which the current is exactly equal to I=ef, where f is the clocking frequency.

While the operation of Coulomb blockade devices has been demonstrated, most operate only at greatly reduced temperatures and require sophisticated nanofabrication procedures. The size scales necessary for Coulomb blockade effects at such relatively elevated temperatures of about room temperature impose limits on the number, uniformity and connectivity of quantum dots. As a result, alternative methodologies of nanofabrication need to be investigated and developed.

The electronic properties of small metallic nanoparticles have been examined for application in nanoelectronics, catalysis, sensors and optics. However, few devices that incorporate such nanoparticles have been developed to date, in large part due to the inability to precisely control the anchoring and positioning of nanoparticles on a substrate. Prior approaches to nanoparticle deposition on surfaces typically have failed to provide the necessary control over nanoparticle size distribution, interparticle spacing, and/or are incompatible with semiconductor processing methods. For at least these reasons, improved electronic transmission grids that can be precisely functionalized are needed.

SUMMARY

Novel TEM substrates comprise a silicon grid with electron transparent $SiO_2$ windows. These grids are smooth as measured by AFM in tapping mode. The RMS roughness of the substrate surface has been measured to be about 0.8 Å±0.08 Å over a 100 nm×100 nm area. Such substrates can be cleaned with, for example, UV/ozone, piranha solution, RCA SC-1 and SC-2 solutions, and oxygen plasma. In addition, surfaces of the $SiO_2$ windows have been chemically modified with self-assembled monolayers and chemically bound nanoparticle arrays. The $SiO_2$ surfaces are robust, cleanable, and amenable to a variety of selective chemical modifications. Such $SiO_2$ surfaces can be used as surfaces on which selected reactions occur, and permit direct images of reaction products using, for example, transmission electron microscopy. Representative examples of reactions that can be obtained and imaged include self-assembly of monolayers and formation of chemically bound nanoparticle arrays.

These TEM grids can be used to, for example, image nanoparticle structures such as a linear array of nanoparticles templated by strands of DNA. DNA can be used as a template to organize close packed arrays of gold nanoparticles and that the spacing between nanoparticles can be controlled by the choice of organic ligand shell on the nanoparticles. In order to make devices, a DNA template is selected, and the strands can be coated with close packed arrays of nanoparticles.

In an example, $SiO_2$ TEM grids were cleaned by UV/ozone for 15 minutes followed by rinsing with ethanol and water, then dried at 60° C. for 1 hr. The clean grids were then silanized overnight by vapor phase deposition of n-octyltrichlorosilane. DNA was aligned on the grids by molecular combing such as developed by Bensimon et al. The DNA arrays were coated with nanoparticles by soaking the grids in thiocholine stabilized 1.4 nm Au-nanoparticles for 20 min. The resulting nanoparticle arrays were rinsed thoroughly with nanopure water and characterized by TEM. The resulting arrays are substantially linear over the entire surface and single strands are substantially linear over the entire length of the DNA molecule. Branching of the DNA may be due to splitting of dsDNA or multiple DNA molecules interacting at the complimentary "sticky ends" of λ-DNA.

In some examples, substrates comprise a silicon layer in which an aperture is defined, wherein the aperture is terminated at a window surface by an electron-transmissive oxide layer. In additional examples, the oxide layer is less than about 100 nm thick or less than about 50 nm thick. The silicon layer can have a thickness of between about 50 μm and 1 mm, and in some examples, an exterior surface of the oxide layer is functionalized by, for examples, silanization. In further examples, an inorganic layer of thickness less than about 50 nm situated on an exterior surface of the oxide layer, or an array of nanoparticles is situated on the exterior surface of the oxide layer at least one window. In other examples, a plurality of apertures are provided on the substrate.

According to representative examples, methods include forming a window layer on at least one surface of a substrate, and exposing the substrate to an etchant to form at least one aperture, wherein an etch rate of the substrate as exposed to the etchant is substantially larger than an etch rate of the window layer as exposed to the etchant. In some examples, a surface of the substrate opposite the window layer is patterned to define a location for the at least one aperture. In other examples, window layers are formed on opposing surfaces of the substrate, and one of the window layers is patterned to pattern the substrate. In additional representative examples, the substrate is silicon and window layers of $SiO_2$ are formed on opposite faces of the substrate. A selected window layer is photolithographically patterned, and the substrate layer is etched based on the photolithographic patterning of the selected window layer so as to define at least one aperture that extends to the other window layer. In some examples, the substrate is about 100 μm thick and the window layers are about 50 nm thick and are formed as a thermal oxide of the substrate layer.

In further representative embodiments, substrates comprise a first window frame region defined in the substrate by a substrate channel. At least one window is defined in the first window region, and at least one tab attaches the first window frame region to the substrate. In some examples, the substrate is a silicon substrate, the window consists essentially of silicon oxide, and the substrate channel extends through the substrate. In additional examples, the window includes at least one electrical conductor situated on a surface of the at least one window. In further examples, the substrate includes a plurality of window frames, each window frame defining a plurality of windows and a plurality of tabs configured so that each window frame is connected by at least one tab to either a different window frame or the substrate. In some examples, a window includes a silicon oxide layer having a thickness of between about 10 nm and 500 nm.

Methods of making a specimen substrate include the steps of defining a window frame in a substrate by thinning the substrate in a channel region and defining an aperture in the window frame, the aperture terminating at a window layer. The window frame is separated from the substrate at the channel region. In representative examples, the window frame is secured to the substrate at least one tab, and the window frame is separated from the substrate by breaking the tab. In further examples, the substrate is silicon, and the aperture is terminated at a silicon oxide layer.

In one embodiment of the disclosure, patterned arrays of nanoparticles are disclosed. In one aspect, such nanoparticle arrays comprise a substrate, an oxophilic metal deposited on the substrate and a linker linking the oxophilic metal to a nanoparticle.

Also disclosed herein is a method for functionalizing surfaces via chemical modification. In one embodiment, the method comprises deposition of an oxophilic metal on an oxidized substrate. In one aspect of this method, a chemically patterned surface can be prepared. For example, in one embodiment, the oxidized substrate is patterned with resist. In this embodiment, deposition of the oxophilic metal results in a chemically patterned surface. Before or after coupling of the oxophilic metal to the oxidized substrate, the metal may be functionalized with a linker molecule, which in turn may be coupled to a nanoparticle. The nanoparticle may be formed before or after coupling to the linker, oxophilic metal and/or substrate. Typically, however, the nanoparticle is synthesized separately, and subsequently is functionalized with the linker and the nanoparticle-linker conjugate is then coupled to the oxophilic metal. However, these array components may be assembled in any order.

Examples of oxidized substrates include those formed via oxidation of coinage metals, such as copper, silver or gold. Another example of an oxidized substrate includes silicon oxide. The oxophilic metal can be any metal with an affinity for the oxidized surface and capable of being functionalized with a linking group. Examples of typical oxophilic metals suitable for functionalizing surfaces as disclosed herein include, without limitation, titanium zirconium and hafnium.

In some embodiments, nanoparticles are coupled to the substrate or to the linker molecule by ligand exchange reactions. In such situations, a nanoparticle, prior to contacting the substrate or linker molecule, typically includes at least one, and more commonly, plural exchangeable ligands bonded thereto. Examples of exchangeable ligands suitable for forming metal nanoparticles may be selected from the group consisting of sulfur-bearing compounds, such as thiols, thioethers (i.e., sulfides), thioesters, disulfides, and sulfur-containing heterocycles; selenium bearing molecules, such as selenides; nitrogen-bearing compounds, such as 1°, 2° and 3° amines, aminooxides, pyridines, nitriles, and hydroxamic acids; phosphorus-bearing compounds, such as phosphines; and oxygen-bearing compounds, such as carboxylates, hydroxyl-bearing compounds, such as alcohols; and mixtures thereof.

The distance between nanoparticles affects the electronic properties of an array of nanoparticles. For example, electron tunneling decays exponentially with distance between nanoparticles. Generally, the scaffold and the nanoparticle ligands define the nanoparticle separation. The scaffold can define the maximum separation of one nanoparticle from a second, and the ligands can define the minimum possible separation of the nanoparticles. For useful tunneling between nanoparticles, the spacing between nanoparticles is provided by ligands comprising a chain typically having from about 2 to about 20 methylene units, with more typical embodiments having the spacing provided by ligands comprising a chain having from about 2 to about 10 methylene units, such that an inter-nanoparticle distance of from about 1 nm to about 30 nm, such as from about 2 nm to about 20 nm, and in certain embodiments from about 5 nm to about 15 nm is provided. Other ligands that yield closely packed nanoparticles, e.g. those that provide an inter-nanoparticle distance of from about 3 Å to about 30 Å, are suitable for making electronic devices.

Electronic devices based on the Coulomb blockade effect also are described that are designed to operate at or about room temperature. Such electronic devices include a first nanoparticle (e.g. a nanoparticle comprising a metal nanoparticle core having a diameter of between about 0.7 nm and about 5 nm) and a second such nanoparticle. In one embodiment, the nanoparticles are physically spaced apart from each other at a distance of less than about 5 nm by coupling the nanoparticles to a scaffold, such as a biomolecular scaffold, for example a protein or nucleic acid having a defined structure, so that the physical separation between the nanoparticles is maintained. In another embodiment, the nanoparticles are spaced apart from about 5 nm to about 200 nm, such as from about 15 to about 80 nm, but typically are spaced apart by from about 1 nm to about 25 nm.

Devices may be manufactured by taking advantage of the well-defined location of various chemical moieties on particular substrates in combination with chemoselective coupling techniques. Thus, different nanoparticle types having different electronic properties and bearing different functional groups can be placed at a particular predetermined location on a scaffold. Particular device features include conductors, inductors, transistors, and arrays of such features; such as to form logic gates and memory arrays.

Because of their unique architecture, electronic devices comprising the nanoparticles described herein exhibit a linear increase in the number of electrons passing between pairs of nanoparticles as the potential difference between the two nanoparticles is increased above a threshold value.

According to some examples, TEM substrates comprise a silicon layer in which an electron-transmissive aperture is defined and an electron transmissive oxide layer is situated in the aperture. In some examples, the oxide layer comprises a metallic oxide and in other examples is at least one of an oxide of at least one of hafnium, aluminum, tin, iron, zinc, and zirconium. In a particular example, the oxide layer comprises indium tin oxide. In further examples, an exterior surface of the oxide layer is functionalized.

According to other examples, substrates comprise a silicon layer and an electron-transmissive aperture layer defined in the silicon layer, wherein the electron-transmissive layer comprises at least one of silicon nitride and silicon oxide and includes at least one functionalized surface. In some examples, the functionalized surface comprises silanols or aryl groups. In additional examples, the functionalized surface comprises aryl groups that include substituents selected from the group comprising nitro groups, esters, alkanes, polyethylene glycols, and halogens. In additional examples, the functionalized surface comprises amines. In other examples, the electron-transmissive layer comprises $Si_3N_4$, and the functionalized surface comprises silanols.

In further embodiments, substrates comprise a silicon layer in which an electron-transmissive aperture is defined and an electron transmissive polymer layer situated in the aperture. In some examples, the electron transmissive polymer layer comprises at least one of a polyvinylchloride, a photoresist, a perfluorinated polymer, a polyester, and a polyalkene. In other examples, the aperture is an etched portion of the substrate.

In other examples, substrates comprise a silicon-containing layer in which an electron-transmissive aperture layer is defined, wherein the aperture layer includes a functionalized surface comprising a hydrophilic moiety, a hydrophobic moiety, or a bifunctional moiety. In typical examples, the functionalized surface comprises a hydrophilic moiety selected from a group comprising alcohols, polyethylene glycols, methoxypoly(ethylene glycol)), carboxylates, and amines. In additional examples, the hydrophilic moiety is secured to the substrate by a linker group moiety. In some examples, the linker is an aliphatic or aromatic hydrocarbon chain and the silicon-containing substrate is $SiO_2$ or $Si_3N_4$. In further examples, the functionalized surface comprises an alkyl hydrophobic moiety. In additional embodiments, the functionalized surface comprises at least one bifunctional moiety selected to attach to the aperture layer and a linker moiety, and the linker moiety is an alkane, alkene, alkyne, or an aromatic moiety. In further examples, the linker moiety includes a reactive functional head group selected from the group comprising amines, thiols, carboxylates, alcohols, phosphines, isonitriles, sulfhydryls, phosphonates, and hydroxyls. In some examples, the bifunctional moiety is a polyethylene glycol that comprises fewer than ten ethylene glycol units.

Methods comprise providing an electron-transmissive window in a substrate and contacting a surface of the electron-transmissive window so as to functionalize the surface. In some examples, the contacting comprises depositing a layer of a polymer or a metal oxide on the surface of the electron-transmissive window. In additional examples, the contacting comprises exposing the surface of the electron-transmissive window to a hydrophobic, hydrophilic, or bifunctional moiety. In further representative examples, the electron-transmissive window is provided by forming a window layer on at least one surface of a substrate, exposing the substrate to an etchant to form at least one aperture, wherein an etch rate of the substrate as exposed to the etchant is substantially larger than an etch rate of the window layer as exposed to the etchant. In other examples, the surface is functionalized by applying a coating by atomic layer deposition, chemical vapor deposition, or as a spin coating.

The foregoing and other features and advantages of the disclosed technology will become more apparent from the following detailed description, which proceeds with reference to the accompanying figures.

BRIEF DESCRIPTION OF THE DRAWINGS

FIGS. 5a-5b are graphs illustrating distributions of interparticle spacing for DNA nanoparticle assemblies formed using normally prepared Au-thiocholine particles and ultrapure Au-thiocholine particles, respectively. (Thiocholine can be abbreviated as "TMAT" for convenience.)

FIGS. 6a-6d illustrate nanoparticle size distributions based on TEM images for normally prepared nanoparticles (FIG. 6a) and ultrapure nanoparticles (FIG. 6b). After assembly on DNA, normally prepared particles grow to 2.7±0.9 nm (n=321) (FIG. 6c), while ultrapure particles become more monodisperse via size selection, having a diameter of 1.4±0.5 nm (n=706) (FIG. 6d).

FIG. 7a illustrates the structure of normally prepared Au-thiocholine assemblies that are generally configured as linear arrays 1-2 nanoparticles wide.

FIG. 7b illustrates the structure of "ribbons" formed with ultrapure particles. The ribbons are typically about 4-5 nanoparticles wide.

FIG. 8a is a schematic diagram of a mask that includes pattern areas for a plurality of grids.

FIG. 8b is a schematic diagram of a representative grid that includes a plurality of $SiO_2$ windows.

FIG. 9b is a schematic diagram of one of the TEM grids of FIG. 9a.

DETAILED DESCRIPTION

Figure 1:
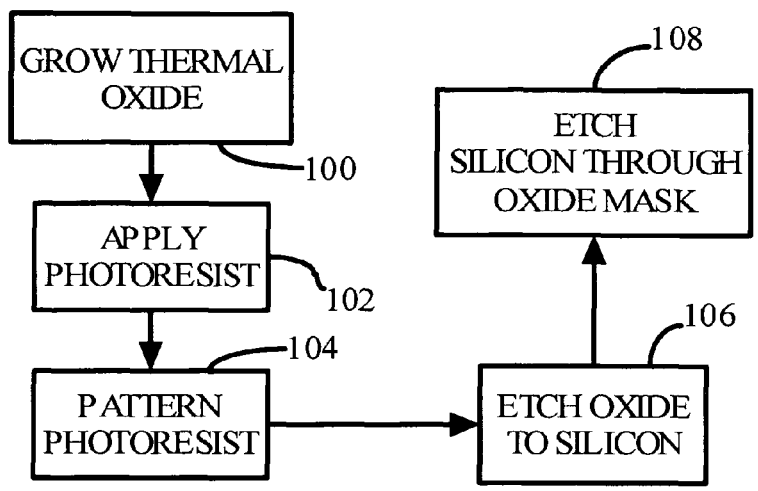
FIG. 1 is a block diagram illustrating a method of making a TEM grid.

As used in this application and in the claims, the singular forms "a," "an," and "the" include the plural forms unless the context clearly dictates otherwise. Additionally, the term "includes" means "comprises." "Optional" or "optionally" means that the subsequently described event or circumstance can but need not occur, and that the description includes instances where said event or circumstance occurs and instances where it does not. The described systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Silicon-Based Grids

Silicon-based TEM grids are described that include electron transparent $SiO_2$ windows. Such TEM grids are useful for investigation of surface chemical interactions on $SiO_2$ and high-resolution TEM imaging of nanostructures assembled on the $SiO_2$ surface. Representative silicon TEM grids can have dimensions similar to those of conventional TEM grids that include 30 μm square windows on a 3 mm diameter substrate, but other substrate and window sizes can be selected. The number and shape of the transmissive $SiO_2$ windows can also be varied. Such silicon-based grids can be chemically treated in the same manner that thermal oxides on silicon are treated and imaged directly without any further sample preparation. The grids can withstand a variety of harsh treatments including exposure to UV radiation, ozone, piranha solution, RCA SC-1 and SC-2 solutions, other cleaning solutions, and oxygen plasma. Chemical reactions on the $SiO_2$ windows of the grids can also be followed by other analytical methods such as XPS or AFM.

Figure 2:
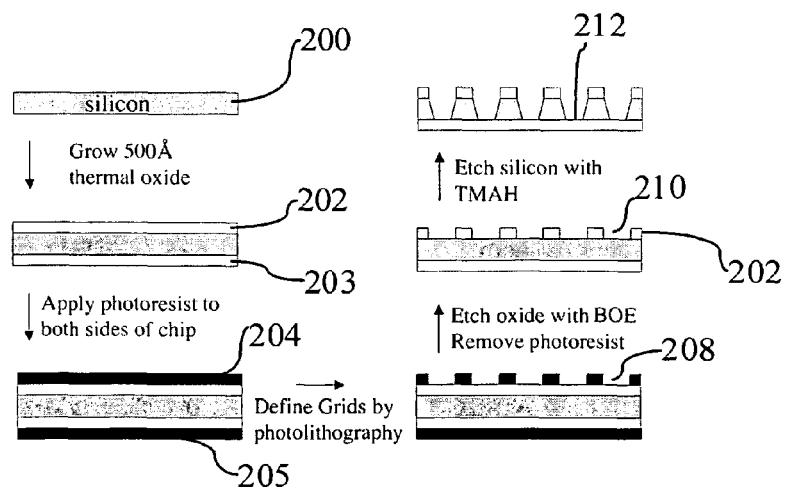
FIG. 2 illustrates a substrate undergoing processing according to the method of FIG. 1.

A representative method of fabricating illustrative examples of the disclosed grids is illustrated in FIGS. 1-2. In a step 100, a 500 Å thermal oxide was grown at 1100° C. under flowing $O_2$ on opposing surfaces of an RCA SC-1 cleaned silicon substrate. Other thicknesses can be selected, but thermal oxide thicknesses are between about 10 Å and 5000 Å, 100 Å and 2500 Å, or preferably between about 200 Å and 2000 Å, or more preferably between about 100 Å and 1000 Å. The silicon substrate was 100 μm thick and was polished on both sides. Thinner or thicker substrates can be used, but substrates having thicknesses of less than about 5 mm are typically convenient. Such substrates are available from, for example, Virginia Semiconductor, Fredericksburg, Va. as ULTRATHIN silicon. In a step 102, both surfaces of the substrate were coated with positive photoresist, and in a step 104, grid patterns were defined by photolithography on one side using a contact mask. In a step 106, exposed portions of the $SiO_2$ layer were etched in a 20:1 buffered oxide etch (BOE) for a time sufficient to etch through the $SiO_2$ layer to a surface of the silicon layer. The photoresist was removed, and the exposed silicon was etched in a step 108 with a 10% (wt %) tetramethylammonium hydroxide (TMAH) solution. The TMAH solution was arranged to be at about 90° C. when etching began, but once the etch was underway, the TMAH solution was cooled to room temperature and allowed to etch through the silicon overnight. The substrate was placed in the TMAH solution "patterned side up" to prevent trapping of gas bubbles in the etching area.

Figures 3A, 3B, 3C, 3D:
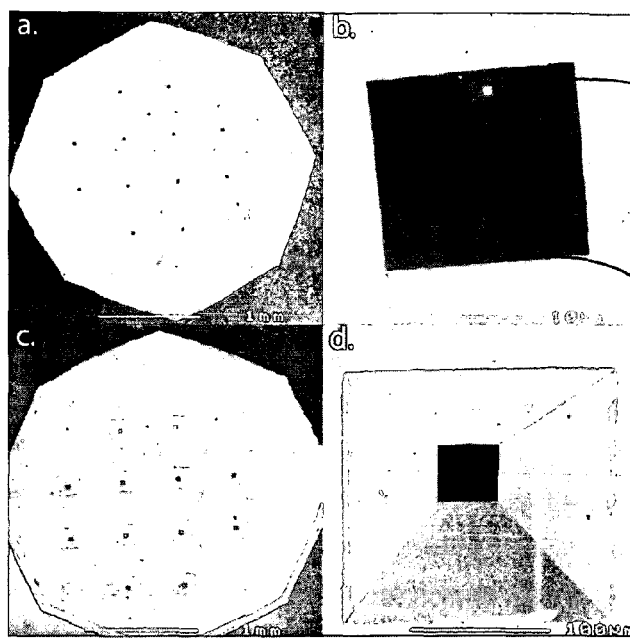
FIG. 3a is a view of a substrate in which an array of $SiO_2$ windows have been formed.
FIG. 3b is an image of a single $SiO_2$ window with a dust particle that verifies that a window layer is present.
FIG. 3c is a back view of the substrate of FIG. 3a showing an array of windows and Si(111) etch planes within the windows.
FIG. 3d is a back view of a single window showing the Si(111) etch planes and residual $SiO_2$ flakes around the larger portion of the window.

As shown in FIG. 8a, a mask 800 such as a photomask has areas that define a plurality of grids in representative pattern areas 802, 804, 806, 808. The mask 800 can be used to define patterned chip areas and can include pattern areas for additional grids or other structures that can be used as desired. A representative grid 810 is shown in FIG. 8b and includes a plurality of $SiO_2$ windows such as a representative window 812. If a ~1.5 cm square chip is used to make the grids, 16 grids (3 mm in diameter each, 4 rows of 4 grids) can be fabricated on one chip. These grids are circular/octagonal as can be seen in FIG. 3a and FIG. 3c, and when the TMAH etches through the chip, the grids separate from the chip into 16 separate grids. As shown in FIG. 8b, the grid includes 12 windows, but different numbers of windows per grid and grids per chip can be used, and the numbers need not be equal. In a representative example, the grids are defined by a mask having pattern areas for 20 grids (4 rows of 5 grids), but only 16 of these grids fit onto a 1.5 cm square chip. With grids defined as shown in FIG. 8a, etching could be conveniently considered as complete when the grids (16 per 1.5 cm square chip) separated from each other. The resulting TEM grids include 16 TEM apertures having a 500 Å thick electron transparent $SiO_2$ windows situated on a silicon substrate.

Typically several silicon substrates are processed, and process yield is sufficient so that about 80 TEM grids can be obtained from 5 silicon substrates having 16 grids per chip. The oxide film is robust, probably due to oxide growth at 1100° C., so that viscous flow of the oxide relieves the compressive stress introduced into the oxide during growth. Therefore, the windows do not tend to buckle or break when the supporting silicon is etched away, and the windows do not appear to be bowed, as there is no evidence of a change in focal plane over the window area. Using the silicon etching conditions described above, grids have most or all oxide windows intact. More aggressive silicon etch conditions, such as maintaining a 90° C. TMAH solution throughout the process, etch faster (~2-3 hrs) but can result in a lower yield of intact windows (1-4) per grid due to turbulence from the rapid production of gas bubbles as the silicon is etched. The grids are durable and easy to handle with tweezers. The windows are robust to harsh processing conditions such as oxygen plasma or swirling in silicon cleaning solutions such as RCA or piranha solutions.

The method of FIG. 1 is further illustrated in FIG. 2. Thermal oxide layers 202, 203 are formed on a silicon substrate 200, and photoresist layers 204, 205 are coated onto the thermal oxide layers 202, 203, respectively. After photolithographic patterning, openings such as the representative opening 208 are formed in the photoresist layer 204. The substrate and patterned photoresist are exposed to an etch suitable for removing thermal oxide, and openings such as the representative opening 210 are formed in the thermal oxide layer 202 so that a patterned thermal oxide layer is formed. The patterned thermal oxide is then used to define exposed portions of the silicon substrate that can be etched with an etch process that does not etch thermal oxide (or slowly etches thermal oxide) so that thermal oxide windows (such as the representative window 212) are formed in the thermal oxide layer 203. In this process, an $SiO_2$ layer is patterned to form a mask for etching the silicon substrate, while a photoresist is used to pattern the $SiO_2$ layer to form the mask. The $SiO_2$ layers serve as an "etch stop" in the silicon etch. Additional process details of a particular process example are set forth further below.

SEM images of representative grids are shown in FIGS. 3a-3d. FIG. 3a shows the generally octagonal shape of a substrate in which 16 $SiO_2$ windows are defined. Although the $SiO_2$ windows are not clearly visible in FIG. 3a, the image of FIG. 3b shows a piece of dust 302 on the $SiO_2$ window to verify the presence of an $SiO_2$ window 304. The octagonal shape is due to anisotropy of the TMAH etch. Images of the back side of the substrate (FIGS. 3c-3d) show the Si(111) etch planes in the window and some residual oxide flakes around the edges.

In one example; these grids are used to assemble aligned, close-packed nanoparticles ($d_{core}$~1.5 nm) on the grids using a three-step assembly process that includes: (i) surface silanization, (ii) DNA molecular combing, and (iii) nanoparticle assembly. These grids permit TEM to be used for investigation of nanoparticle size, spacing, and coverage on the same substrate used for the assembly reaction. TEM investigation of the assemble nanoparticles shows that nanoparticle purity has a significant effect on the resulting structures. Conventional grids or other analytical methods such as AFM or SEM would not permit such analysis or provide data for such a conclusion.

In a representative application of the silicon grids with electron-transparent $SiO_2$ windows described above, the $SiO_2$ window surfaces were chemically modified and DNA was aligned on the chemically modified surfaces to direct the assembly of linear arrays of nanoparticles. With nanoparticle arrays on the electron-transparent windows, TEM could be used to quantify the effects of assembly conditions on nanoparticle size, spacing, and dispersity in the arrays.

In solution, DNA can be used as a template to organize close packed arrays of gold nanoparticles and the spacing between nanoparticles can be controlled by the choice of organic ligand shell on the nanoparticles. See M. G. Warner and J. E. Hutchison, *Nat. Mater.* 2003, 2, 272-277. In order to make devices from these arrays, the assembly process can be executed directly on surfaces. First, the DNA template is positioned on a chemically-modified surface, and second, close-packed arrays of nanoparticles are assembled on these surface bound DNA scaffolds. While a two-step process of aligning DNA followed by coating with positively charged nanoparticles has been reported (see N. Hidenobu et al., *Nano Lett.* 2003, 3, 1391-1394), the arrays produced in this way were characterized by AFM, and individual nanoparticles were not resolved. Therefore, the nanoparticle size distribution, interparticle spacing, and overall coverage could not be determined. $SiO_2$/Si grids as described above are excellent substrates for the investigation of this surface-based assembly chemistry by TEM, and permit measurement of nanoparticle size distribution, interparticle spacing, and overall coverage.

Silanization of the grids and DNA alignment were performed as described by A. Bensimon et al, *Science* 1994, 265, 2096-2098. The grids were cleaned by a 15 min UV/ozone treatment followed by rinsing with ethanol and ultrapure water, dried at 60° C. for 1 hr, then put in a desiccator with a beaker containing 300 µL n-octyltrichlorosilane for 18 hrs. This vapor phase silanization was performed at room temperature and pressure. The silanized grids were rinsed with ultrapure water to hydrolyze any remaining Si—Cl bonds. The grids were incubated in a solution of λ-DNA (5 µg/mL) in MES buffer (pH=5.5) for 5 min at room temperature, then pulled from solution at 300 µm/s as described in X. Michalet et al., *Science* 1997, 277, 1518-1523. The DNA arrays were rinsed thoroughly with ultrapure water, then soaked in a solution of Au-thiocholine nanoparticles (1 mg/mL) for 20 min. In order to observe DNA on only one side of the TEM grid, the nanoparticle soak was performed by placing a 10 µL drop of nanoparticle solution on the top side of the grid. The hydrophobic silanized surface prevents the drop from spreading beyond the edge of the grid. Upon completion of the assembly process, the grids were rinsed thoroughly with ultrapure water to remove any nonspecifically bound nanoparticles.

Nanoparticles were synthesized as described previously. Briefly, $HAuCl_4$ in $H_2O$ reacts with triphenylphosphine (TPP) in toluene in the presence of the phase transfer catalyst tetraoctylammonium bromide. Reduction with $NaBH_4$ yields ~1.5 nm TPP stabilized nanoparticles. (2-mercaptoethyl)trimethylammonium iodide (thiocholine) was synthesized. A biphasic ligand exchange between thiocholine in $H_2O$ and the TPP-stabilized nanoparticles in $CH_2Cl_2$ yielded positively charged, water-soluble Au-thiocholine nanoparticles. See M. G. Warner et al., *Chem. Mater.* 2000, 12, 3316. The thiocholine stabilized nanoparticles were purified by two rounds of ultracentrifugation at 55,000 rpm. A subset of these Au-thiocholine nanoparticles was further purified by diafiltration (10 volumes, 10 kD) to achieve 'ultrapure' Au-thiocholine nanoparticles.

Figure 4A:
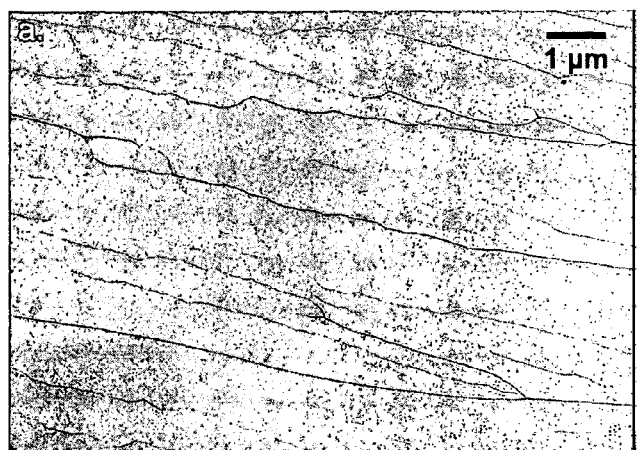
FIGS. 4a-4b are TEM images of DNA templated nanoparticle arrays.
Figure 4B:
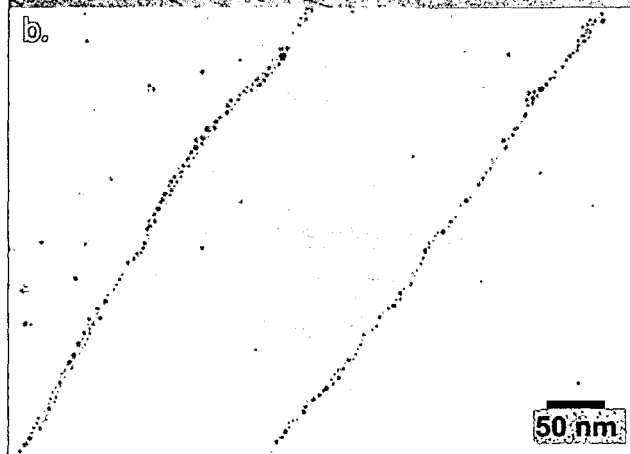

Chemical functionalization of the $SiO_2$ surface with n-octyltrichlorosilane is a significant consideration for this assembly process as the silanized surface promotes molecular combing of DNA and limits nonspecific adsorption of the positively charged nanoparticles. Low-resolution images (FIG. 4a) show that the nanoparticles form linear, parallel arrays over the entire surface of the substrate. Higher resolution images (FIG. 4b) show that the nanoparticles are close-packed over the entire DNA molecule with an average interparticle spacing of 1.5±0.8 nm (n=353) for the Au-thiocholine particles (FIG. 5a) and 1.4±0.5 nm (n=398) for the ultrapure Au-thiocholine particles (FIG. 5b). An average spacing of 1.4 nm is expected assuming that the particles are close-packed and that the Au-core spacing is dependent on the thickness of the thiocholine ligand shell.

Prior to deposition on DNA, the nanoparticle size distributions were 1.7±0.7 nm (n=792) for the Au-thiocholine particles (FIG. 6a) and 1.7±0.6 nm (n=1476) for the ultrapure Au-thiocholine particles (FIG. 6b). Both appear to have a bimodal distribution that is more pronounced for the normally prepared particles. Interestingly, after deposition on DNA, the Au-thiocholine particles grew to 2.7±0.9 nm (n=321) (FIG. 6c) while the ultrapure Au-thiocholine particles apparently decreased in size to 1.4±0.5 nm (n=706) (FIG. 6d). Particle size distributions and interparticle spacings were analyzed using NIH ImageJ for MacIntosh computers. Particle size was measured as the average of the major and minor axes. The decrease in average diameter and increase in monodispersity of the ultrapure particles on DNA may be a result of size selection toward smaller particles that presumably have a higher charge density than larger particles due to their higher surface to volume ratio.

The difference in the assemblies formed from the normally prepared nanoparticles and ultrapure nanoparticles is surprising. The notable difference between the samples is that the normally prepared Au-thiocholine samples contain traces of free thiocholine ligand associated with the nanoparticles that can be seen as small differences in the NMR spectra. High concentrations of free ligand have been known to destabilize nanoparticles during ligand exchange reactions. See G. H. Woehrle et al., *Langmuir* 2005, 127, 2172-2183. The increased size of the Au-thiocholine particles may be due to concentration of free ligand near the DNA, resulting in nanoparticle growth on the DNA backbone.

The structures of the normally prepared Au-thiocholine assemblies and the ultrapure Au-thiocholine assemblies are also qualitatively different. The Au-thiocholine particles form linear arrays 1-2 nanoparticles wide (FIG. 7a) while the ultrapure particles form "ribbons" 4-5 nanoparticles wide (FIG. 7b). Some examples of ribbons from solution phase assemblies appear to result from the multivalent character of the positively charged nanoparticles cross-linking several DNA strands, but this should not be the case for the ribbons of FIG. 7b, as the DNA scaffolds are aligned prior to the addition of nanoparticles. Another possibility is that higher order DNA structures such as DNA bundles were aligned on the grid used for the ultrapure particle assemblies. However, all of the DNA assemblies were prepared from the same DNA solution and the same silanization conditions. These differences were reproducible on four grids for each of the two types of nanoparticles, which suggests that the structural differences are not due to differences in the DNA scaffolds. The most plausible explanation is that the normally prepared Au-thiocholine particles also form the ribbon structures, but grow together to form the linear arrays. This could account for both the increase in particle size and decrease in width of the normally prepared particles.

Process Example

For purposes of illustration, a representative process is described in further detail below. A 500 Å thermal oxide was grown at 1100° C. under flowing $O_2$ on an RCA cleaned chip cut from a 100 µm thick 2" silicon Ultra Thin™ wafer polished on both sides (Virginia Semiconductor, Fredericksburg, Va.). The chips were coated with a positive photoresist (Shipley S1818) by spin coating at 5000 rpm for 30 s followed by a 1 min soft bake at 100° C. The chips were coated on both sides and the grids were defined by UV photolithography on one side using a contact mask. After developing (Shipley 351 developer) and hard baking the photoresist at 120° C. for 30 min, the exposed $SiO_2$ was etched for 3 min in 20:1 BOE (Buffered Oxide Etch, 20:1, J. T. Baker). (Buffered oxide etch, 20:1 refers to a solution consisting of 20 parts ammonium fluoride (40%) to 1 part HF (49%).) The photoresist was removed by sonication in acetone followed by an ultrapure water rinse. The chips were then dipped briefly (5 seconds) in 20:1 BOE to remove any oxide that may have formed during the photoresist removal, and rinsed with ultrapure water. The exposed silicon was etched with 10% (wt %) TMAH solution initiated at 90° C. Once it was clear that the etch was underway, the solution was cooled to room temperature and allowed to etch through the silicon overnight. The chips were placed in the solution "patterned side up" to prevent trapping gas bubbles in the etching area. The etch was considered complete when the grids separated from each other. This resulted in TEM grid shaped silicon discs with 500 Å thick electron transparent windows of $SiO_2$ on one side.

Nanoparticles were synthesized as follows. Briefly, $HAuCl_4$ in $H_2O$ reacts with triphenylphosphine (TPP) in toluene in the presence of the phase transfer catalyst tetraoctylammonium bromide. Reduction with $NaBH_4$ yields TPP stabilized nanoparticles. (Hutchison, J. E.; Foster, E. W.; Warner, M. G.; Reed, S. M.; Weare, W. W.; Buhro, W.; Yu, H. *Inorganic Syntheses* 2004, 34, 228-232.) Thiocholine was synthesized as described previously. (Warner, M. G.; Hutchison, J. E. *Nature Mater.* 2003, 2, 272) A biphasic ligand exchange between thiocholine in $H_2O$ and the TPP stabilized nanoparticles in $CH_2Cl_2$ yielded positively charged, water-soluble nanoparticles. (Warner, M. G.; Reed, S. M.; Hutchison, J. E. *Chem. Mater.* 2000, 12, 3316)

The grids were cleaned by a 15 min. UV/ozone treatment followed by rinsing with ethanol and ultrapure water. The grids were dried at 60° C. for 1 hr, then put in a dessicator with a beaker containing 300 µL n-octyltrichlorosilane overnight. This vapor phase silanization was performed at room temperature and pressure. The silanized grids were rinsed with ultrapure water to react any remaining Si—Cl bonds. The grids were incubated in a solution of λ-DNA (5 µg/mL) in MES buffer (pH=5.5) for 5 min. at room temperature, then pulled from solution 300 µm/s. The grids were then soaked in a solution of thiocholine stabilized 1.4 nm Au-nanoparticles (2.4 mg/mL) for 20 min. In order to observe DNA on only one side of the TEM grid, the nanoparticle soak was performed on only one side of the grid by placing a 10 µL drop of nanoparticle solution on the top side of the grid. The hydrophobic silanized surface prevents the drop from spreading beyond the edge of the grid.

The above representative process example can be modified in arrangement and detail, and is provided to further illustrate aspects of the disclosed technology.

$SiO_2$ TEM grids can be used for imaging chemically functionalized $SiO_2$ surfaces ranging from nanoelectronics and photonics to MEMS, and the application described above is a convenient, representative application. Because such grids are fabricated from thermal oxides, they can be used to understand chemistry and assembly on $SiO_2$ without time consuming and destructive sample prep methods. There is little ambiguity as to how closely the substrate approximates $SiO_2$, there is no need for time-consuming sample preparation, and the images are high resolution. Such substrates can be used to investigate surface chemistry, nanoparticle chemistry, and alignment methods, and other factors associated with DNA/nanoparticle arrays and structures on thermal oxides, including two dimensional arrays of nanoparticles chemically bound to the $SiO_2$ surfaces.

The $SiO_2$ surfaces of these grids can be functionalized in other ways. In some examples, functionalization is directed to fabrication of micro- or nanoscale electrodes on the grids to, for example, take advantage of TEM imaging and analysis of the electrodes and structures within the electrode gaps. Silanization of these grids permits a wide range of surface modifications using organic species. The $SiO_2$ surface can be functionalized with inorganic species by, for example, atomic layer deposition or other suitable deposition techniques such as evaporation, sputtering, or chemical vapor deposition. For example, Au, Hf, or other metal layer, metal layers, or partial metal layer can be situated on a grid surface. Other functionalizations can be used such as, for example, hafnium-phosphonate functionalizations, and can be based on metals, metal oxides, or organic compounds.

In typical examples, $SiO_2$ window thickness is selected for electron transparency, and thicknesses less that about 200 nm provide superior transmission. The supporting silicon substrate is typically between about 50 µm and 1 mm thick, but other thickness can be used. $SiO_2$ window sizes can be varied as well. Silicon is a convenient substrate due to the availability of silicon selective etches for which the $SiO_2$ window layer serves as an etch stop layer. In typical convenient processes, a silicon layer is etched to form apertures that are terminated at an end with an $SiO_2$ window.

Window thickness can be critical to obtaining the highest resolution images. To further improve available resolution, thinner windows can be produced. In some cases, windows can be thinned after wet chemical processing is done. For example, the windows can be further thinned by dry etching, even to the point of making the windows "holey," like holey carbon films. If the thinning is done from the interior, exterior surface chemistry of the silicon dioxide layer or a derivatized version of it can remain unaltered.

Figure 9A:
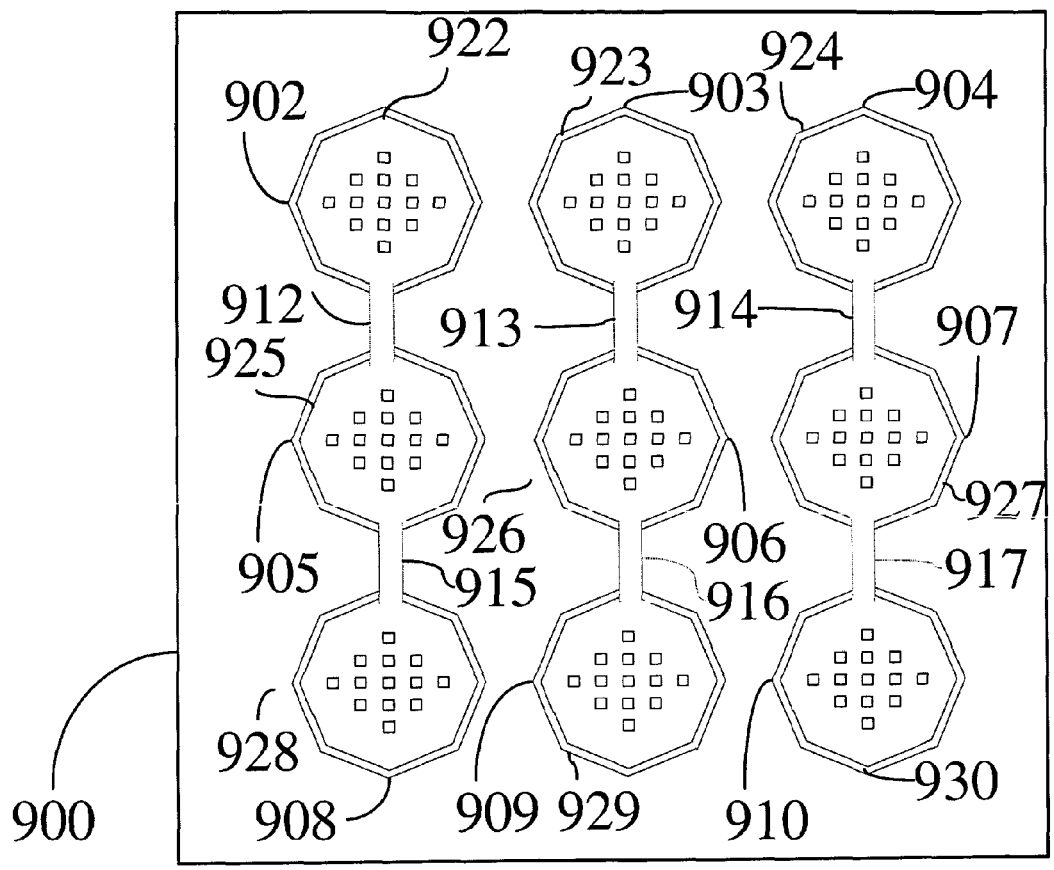
FIG. 9a is a schematic diagram of a silicon substrate on which a plurality of TEM grids are defined.
Figure 9B:
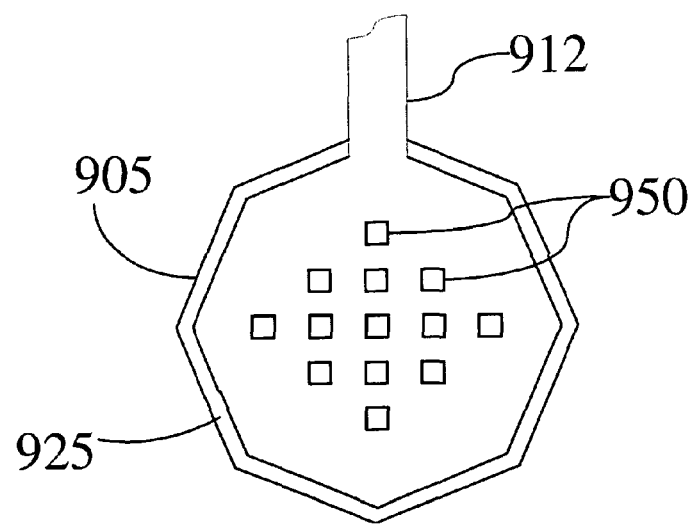

TEM grids such as those described above can be fabricated in sets as shown in FIGS. 9a-9b. Referring to FIG. 9a, a substrate 900 is used to define TEM grids 902-910 that are secured to the substrate 900 with tabs 912-917. The TEM grid 905 is shown enlarged in FIG. 9b. The substrate 900 is typically a silicon substrate, and the TEM grids 902-910 are separated from the substrate 900 with respective channels 922-930. For silicon substrates, the channels 922-930 can be defined by etching the substrate. For example, the channels can be defined by etching a silicon substrate down to an oxide layer in a manner similar to that used to define the TEM grids as described above so that perimeters of the TEM grids 902-910 are attached to the substrate 900 by an oxide layer and/or one or more tabs. Alternatively, the channels can be completely etched through the silicon substrate and the oxide layer, leaving the TEM grids 902-910 attached to the substrate 900 only at the tabs. The tabs can be unetched or partially etched portions of the substrate 900. For example, the tabs can be associated with portions of the substrate that are etched down to an oxide layer, or partially etched toward an oxide layer. As shown in FIGS. 9a-9b, each TEM grid is shown with two oppositely situated tabs, but one or more tabs can be used, and tabs can be arbitrarily situated at the perimeters of the TEM grids.

The processed substrate of FIG. 9a provides a convenient support for additional substrate processing. For example, conductors can be defined on one or more of the TEM grid windows using conventional photolithographic or other techniques. During the necessary processing steps (such photoresist coating, photoresist patterning, resist development, metal deposition, resist lift off etc.), the TEM grids remain attached to the substrate, and are removed from the substrate upon process completion. The substrate 900 can be large enough for convenient handling (typical dimensions of between about 20 mm and about 250 mm or larger) in contrast to the few mm dimensions of the TEM grids. For electrical investigations of samples situated on an oxide window, electrically conductive materials can be deposited on either window surface. In typical examples, gold conductor lines are defined on the window exterior and not within the recess defined by etching a substrate down to the oxide layer. Conductor lines can be defined using photolithographic or other processes, and the relatively large size of the substrate facilitates such processing.

Figure 10:
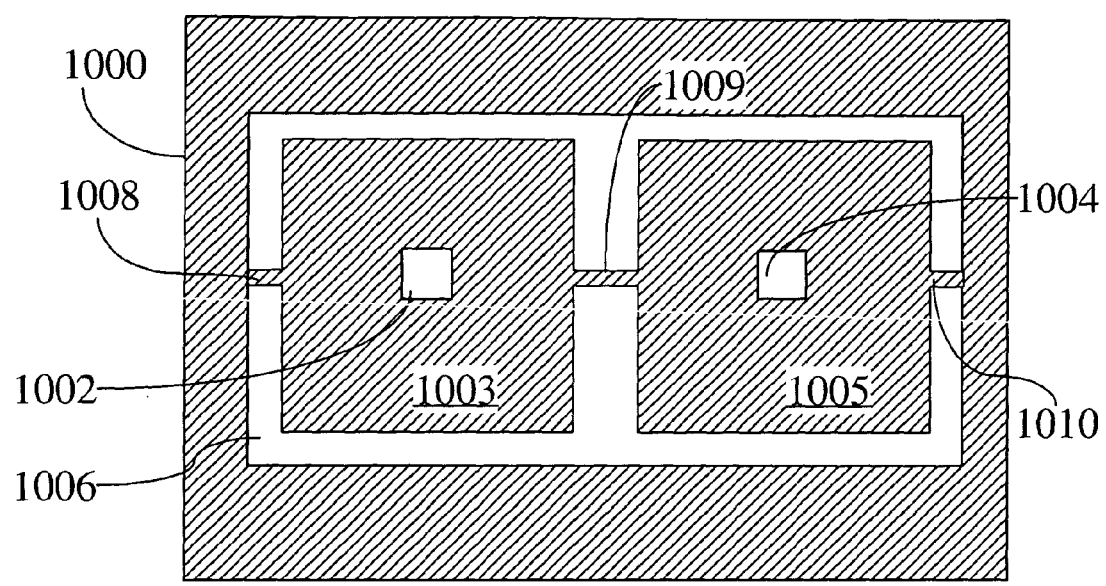
FIG. 10 is a schematic diagram of a substrate that includes a first window and a second window that are defined as apertures in the substrate or as thinned portions of the substrate.
Figure 11:
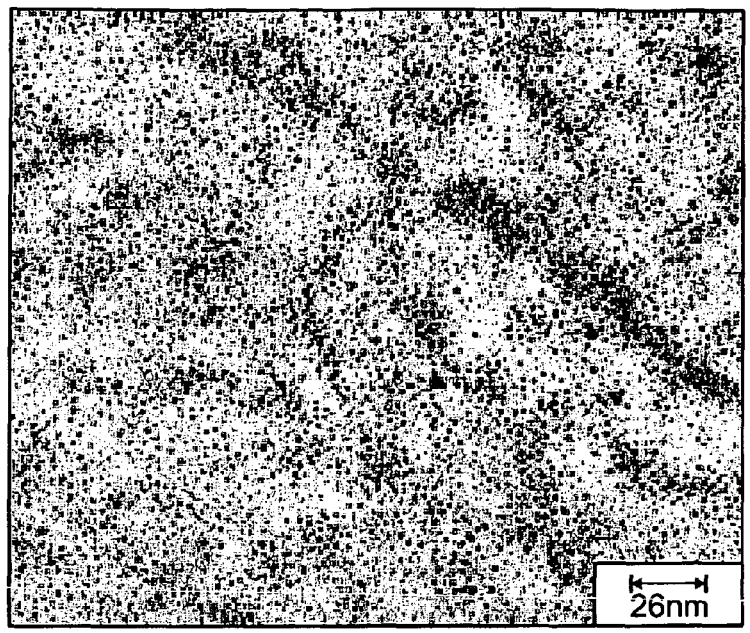
FIG. 11 is a representative TEM micrograph of a gold nanoparticle assembly formed on silicon dioxide.
Figure 12A:
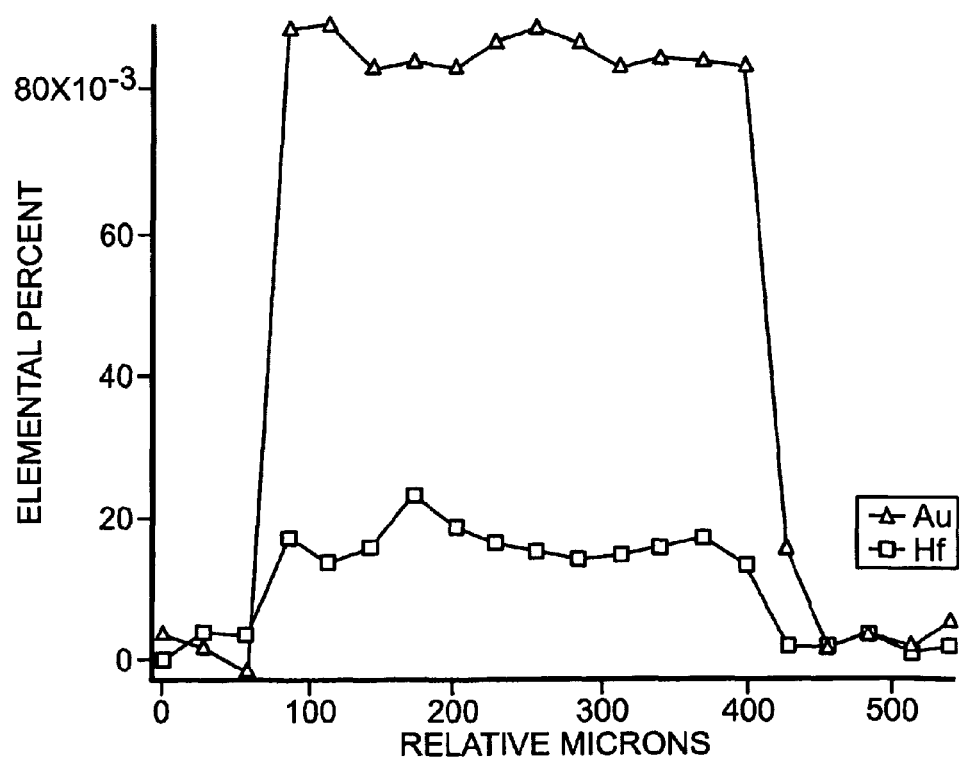
FIG. 12a is an electron probe microanalyzer (EPMA) line scan over a 300 µm patterned square, wherein Au and Hf were only observed in functionalized areas.
Figure 12B:
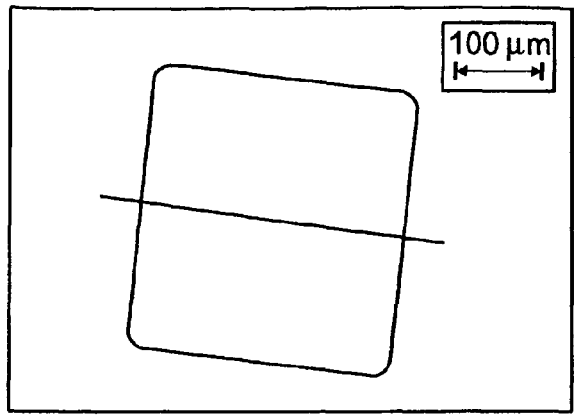
FIG. 12b contains a representation of an SEM backscatter image of a patterned square, wherein an area enclosed by the patterned square appears brighter than a background area indicative of higher electron density in the patterned area. The line across the square illustrates the path of a typical EPMA line scan.

While TEM grids that include a plurality of TEM transmissive windows can be provided as shown in FIGS. 9a-9b, a single window can be provided such that the single window remains attached to a larger substrate by one or more tabs. An array of single windows can be provided with tabs so that the single windows are individually separable, but are part of a large substrate for convenient processing such as, for example, formation of one or more conductors on one or more windows. For example, referring to FIG. 10, a substrate 1000 includes a first window 1002 and a second window 1004 that are defined as apertures in the substrate 1000 or thinned portions of the substrate 1000. Such thinned portions can terminate in thinned layers of substrate oxides or nitrides having typical thicknesses of between about 10 nm and 500 nm. For example, the windows can be defined as apertures terminating in silicon oxide or nitride layers. In other examples, different substrate materials and window termination materials can be used.

The windows 1002, 1004 are defined in frames 1003, 1005 that are attached to the substrate 1000 with tabs 1008, 1010 and that are separated from the substrate by a channel 1006. The channel can extend completely or partially through the substrate 1000, or can terminate in the same way as the windows 1002, 1004 with, for example, silicon oxide or silicon nitride.

Functionalization

The following abbreviations and definitions are provided to facilitate understanding of the disclosed technology but not to define terms to have a scope narrower than would be understood by a person of ordinary skill in the art.

Certain abbreviations used include:

| | |
|---|---|
| PL | polylysine |
| PLL | poly-L-lysine |
| AFM | atomic force microscopy |
| TEM | transmission electron microscopy |
| SEM | scanning electron microscopy |
| PMMA | polymethyl methacrylate |
| XPS | X-ray photoelectron spectroscopy |
| ODT | octadecylthiol |
| TOABr | tetraoctylammonium bromide |

An overview of an embodiment of the process used to produce organized arrays comprising metal, alloy, semiconductor and/or magnetic nanoparticles includes (1) coupling molecular scaffolds to substrates, generally a metal, glass or semiconductor material having an oxidized surface, in predetermined patterns, (2) forming substantially monodisperse, relatively small (Coulomb blockade effects are dependent upon nanoparticle size, e.g., metal particles having a diameter of less than about 2 nm exhibit Coulomb blockade behavior at room temperature) ligand-stabilized metal, alloy, semiconductor and/or magnetic nanoparticles, (3) coupling the ligand-stabilized nanoparticles to the scaffolds to form organized arrays, (4) coupling electrical contacts to the organized arrays, and (5) using such constructs to form electronic, particularly nanoelectronic, devices. Alternatively, nanoparticles can be coupled to scaffolds prior to coupling the scaffolds to substrates.

Certain of the following passages therefore describe how to make and use devices based on metal nanoparticle arrays. Unless expressly stated otherwise, or the context indicates differently, it should be understood that any reference in this application to "metal nanoparticles" or "nanoparticles" typically refers to metal nanoparticles, alloy nanoparticles, semiconductor nanoparticles, magnetic nanoparticles, and combinations thereof.

Nanoparticles are so termed because the size of each such nanoparticle is on the order of about one nanometer. Typically, nanoparticles have a diameter of less than about one micron. In terms of diameters, "nanoparticle" is defined herein as having a diameter ($d_{core}$, not including the ligand sphere) of from about 0.7 nm to about 5 nm (7 Å to about 50 Å), for example, from about 0.7 nm to about 2.5 nm (7 Å to about 25 Å), and more typically from about 0.8 nm to about 2.0 nm (8 Å to about 20 Å).

It currently is believed that nanoparticles having diameters much larger than about five nanometers are less useful for forming electronic devices that operate on the Coulomb blockade principle at or about room temperature. Accordingly, in certain embodiments, the nanoparticle core, considered without any accompanying ligands, typically will have a diameter ($d_{core}$) of less than about 5 nm. More typically $d_{core}$ of the nanoparticles described herein is less than about 2 nm. In one embodiment, the $d_{core}$ is from about 0.7 to about 1.4 nm. Certain embodiments employ $Au_{11}$ nanoparticles having a diameter of about 0.8 nm.

In other embodiments, larger nanoparticles are used, for example, nanoparticles having a $d_{core}$ of larger than about 5 nm are useful for certain applications, including optical applications, such as forming wave guides. In one embodiment such large nanoparticles have a $d_{core}$ of from about 10 to about 170 nm, such as from about 15 to about 80 nm.

Particular embodiments used nanoparticles having a diameter including the ligand sphere of from about 0.8 nm to about 2 nm. Such nanoparticles included, without limitation those having diameters of 0.8±0.2 nm, 1.1±0.3 nm, 1.2±0.3 nm, 1.3±0.4 nm and 1.9±0.7 nm.

"Substantially monodisperse" with respect to present embodiments means particles having substantially the same size. The useful conducting properties of the arrayed nanoparticles diminish if the particle size distribution comprises greater than about a 30% polydispersity calculated at two standard deviations. Thus, a collection of substantially monodisperse nanoparticles should have less than about a 30% dispersion for the purposes of present embodiments. The $Au_{11}$ nanoparticles described herein are substantially completely monodisperse, meaning that they are monodisperse as judged by all analytical techniques employed to date. If the nanoparticles are metal nanoparticles, then the metal may be selected from the group consisting of Ag, Au, Pt, Pd, Co, Fe and mixtures thereof. The metal nanoparticle may have a $d_{core}$ of from about 0.7 nm to about 5 nm. Particular working examples comprise gold nanoparticles having average diameters of about 1.4-1.5 nm, which traditionally have been referred to as $Au_{55}$ nanoparticles. Additional working examples employ $Au_{11}$ nanoparticles, which have a diameter of about 0.8 nm. Useful compositions for forming patterned arrays of metal, alloy, semiconductor and/or magnetic nanoparticles are provided below. Additional compositions useful in the present method are disclosed in U.S. Patent Application Publication No. 2003/0077625, published Apr. 24, 2003, and U.S. Pat. No. 6,730,537, which are incorporated herein by reference.

An "array" is an arrangement of plural such nanoparticles spaced suitably from one another for forming electronic components or devices. The spacing should be such as to allow for electron tunneling between nanoparticles of the array. Examples include lower order arrays, such as one-dimensional arrays, one example of which comprises plural nanoparticles arranged substantially linearly. Plural such arrays can be organized, for example, to form higher order arrays, such as a junction comprising two or more lower order arrays. A higher order array also may be formed by arranging nanoparticles in two or three dimensions, such as by coupling plural nanoparticles to two- or three-dimensional scaffolds, and by combining plural lower order arrays to form more complex patterns, particularly patterns useful for forming electronic devices. Features of embodiments of the present method include, both individually and in combination, the small physical size of the metal nanoparticles, the substantial monodispersity or monodispersity of the nanoparticles, the ligand exchange chemistry and/or the nature of the ligand shell produced by the ligand exchange chemistry. The small physical size of the metal nanoparticles provides a large Coulomb charging energy. The ligand-exchange chemistry allows tailoring of the ligand shell for a particular purpose and immobilize the nanoparticles on biomolecules. And, the ligand shell offers a uniform and chemically adjustable tunnel barrier between nanoparticle cores.

The following paragraphs describe particular embodiments and applications in greater detail.

I. Forming Substantially Monodisperse Ligand-Stabilized Nanoparticles

One aspect of the present disclosure includes the recognition that substantially monodisperse, relatively small metal nanoparticles can be used to develop electronic devices that operate at or about room temperature based on the Coulomb blockade effect.

The term "nanoparticles" as used herein refers to more than one, and typically three or more, metal, alloy, semiconductor or magnetic atoms, typically coupled to one another, such as either covalently, ionically or both. Nanoparticles are intermediate in size between single atoms and colloidal materials. As discussed above, a goal is to provide electronic devices that operate at or about room temperature. This is possible if the nanoparticle size is made small enough to meet Coulomb blockade charging energy requirements at room temperature. While nanoparticle size itself is not dispositive of whether the nanoparticles are useful for forming devices operable at or about room temperature, nanoparticle size is nonetheless a factor.

Prior approaches typically have used polydisperse metal nanoparticles wherein the size of the metal nanoparticles is not substantially uniform. A completely monodisperse population is one in which the size of the metal nanoparticles is identical as can be determined by currently used characterization procedures. However, complete monodispersity is difficult, if not impossible, to achieve in most sizes of nanoparticles. Although complete monodispersity is not required to produce devices operating at or about room temperature based on the Coulomb blockade effect, as the dispersity of the nanoparticle population proceeds from absolute monodispersity towards polydispersity the likelihood that the device will operate reliably at room temperature, based on the Coulomb blockade effect, decreases. For example, $Au_{11}$ nanoparticles prepared as described herein are virtually completely monodisperse. However, 1.4-1.5 nm diameter gold nanoparticles are not as monodisperse as $Au_{11}$ particles, which have a diameter of about 0.8 nm. Moreover, as the radius of the metal nanoparticle decreases, the intrinsic capacitance gets smaller. As capacitance gets smaller, the charging energy of the nanoparticle gets larger. Coulomb blockade effects are observed when the charging energy exceeds the thermal energy at room temperature. Prior approaches have used nanoparticles that are generally larger than would be useful for forming devices that operate at room temperature based on the Coulomb blockade effect. In contrast, the present method forms metal nanoparticles having relatively small diameters.

With its ligand shell, the diameter of the ligand-stabilized metal nanoparticle can vary. The size of the ligand shell may influence the electron-tunneling rate between nanoparticles. Tunneling rate is exponentially related to the thickness of the ligand shell. As a result, the diameter of the ligand shell may be tailored for a particular purpose. It currently is believed that the diameters for ligand-stabilized nanoparticles useful for preparing electronic devices should be from about 0.8 nm to about 5 nm. The relatively large metal nanoparticles made previously do not provide a sufficiently large Coulomb charging energy to operate at room temperature. Instead, prior known materials generally only operate at temperatures of from about 50 mK to about 10 K.

"Bare" nanoparticles, i.e., those without ligand shells, also may be useful for preparing particular embodiments of electrical devices. For example, bare nanoparticles can be used to form electrical contacts.

Still another consideration is the distance between the edges of metal nanoparticle cores. It currently is believed that the maximum distance between the edges of nanoparticle cores for useful nanoparticles is about 5 nm (50 Å), and ideally is on the order of from about 1 to about 2 nm (10-20 Å).

In certain embodiments, the nanoparticle ligands are selected such that a nanoparticle density on the substrate is from about 200 to about 2000 nanoparticles per 100 nm×100 nm area, such as from about 400 to about 1600 nanoparticles per 10,000 $nm^2$ area. In certain embodiments the nanoparticle density is from about 500 to about 800 nanoparticles per 10,000 $nm^2$ area. Of course these densities are for a monolayer, a two-dimensional array of nanoparticles. Similar nanoparticle spacing also is present in, for example, one-dimensional arrays, such as lines formed using the nanoparticles.

Solely by way of example, metals used to form ligand-stabilized metal nanoparticles may be selected from the group consisting of silver (Ag), gold (Au), platinum (Pt), palladium (Pd), cobalt (Co), iron (Fe), and mixtures thereof "Mixtures thereof" refers to having more than one type of metal nanoparticle coupled to a particular scaffold, different metal nanoparticles bonded to different scaffolds used to form a particular electronic device, or having different elements within a nanoparticle. Thus it is possible that metal alloy nanoparticles, e.g., gold/palladium nanoparticles, can be used to form nanoparticle arrays and electronic devices.

Gold is a particularly useful metal for forming ligand-stabilized monodisperse metal nanoparticles. This is because (1) embodiments of the present method of gold nanoparticle ligand exchange chemistry conveniently provides well-defined products, (2) $Au_{11}$ has a diameter of about 0.8 nm and $Au_{55}$ has a diameter of about 1.4 nm, making these particles particularly useful for forming organized metal arrays that exhibit the Coulomb blockade effect at or about room temperature, and (3) it is possible to prepare nearly monodisperse gold nanoparticles without lengthy purification requirements, such as lengthy crystallization processes.

Nanoparticles comprising semiconductor materials also may be useful for preparing electronic devices. Semiconductor materials that may be prepared as nanoparticles and stabilized with ligand spheres include, without limitation, cadmium selenide, zinc selenide, cadmium sulfide, cadmium telluride, cadmium-mercury-telluride, zinc telluride, gallium arsenide, indium arsenide and lead sulfide.

Magnetic particles also may be used to decorate scaffolds to provide structures having useful properties. An example, without limitation, of such magnetic particles is iron oxide ($Fe_2O_3$).

II. Ligands

A. Background

Once a suitable metal, alloy, semiconductor and/or magnetic material is selected for forming desired nanoparticles, ligands for bonding to the nanoparticles also must be selected. The assembly of nanoparticles into structures suitable for nanoelectronic applications, e.g., Coulomb blockade, involves molecular-scale organization of the nanoparticles without destroying the insulating ligand sphere between individual nanoparticles. The nanoparticles also should be coupled to the substrate in a sufficiently robust manner to allow fabrication of devices incorporating nanoparticle arrays. This may be accomplished in certain instances by ligand exchange reactions. The selection of ligands for forming an insulating ligand layer about the nanoparticle and for undergoing ligand exchange reactions therefore is a consideration. Criteria useful for selecting appropriate ligands include, but are not limited to, (1) the ligand's ability to interact with the substrate and/or oxophilic metal deposited thereon, such as through ligand-exchange, coulombic, intercalative, or covalent bond-forming interactions, (2) solubility characteristics conferred upon the ligand-metal nanoparticle complexes by the ligand, and (3) the formation of well ordered, metal-ligand complexes having structural features that promote room temperature Coulomb-blockade effects.

B. Classes of Ligands

Ligands suitable for forming metal nanoparticles may be selected, without limitation, from the group consisting of sulfur-bearing compounds, such as thiols, thioethers, thioesters, disulfides, and sulfur-containing heterocycles; selenium bearing molecules, such as selenides; nitrogen-bearing compounds, such as 1°, 2° and perhaps 3° amines, aminooxides, pyridines, nitriles, and hydroxamic acids; phosphorus-bearing compounds, such as phosphines; and oxygen-bearing compounds, such as carboxylates, hydroxyl-bearing compounds, such as alcohols, and polyols; and mixtures thereof. Particularly effective ligands for metal nanoparticles may be selected from compounds bearing elements selected from the chalcogens. Of the chalcogens, sulfur is a particularly suitable ligand, and molecules comprising sulfhydryl moieties are particularly useful ligands for stabilizing metal nanoparticles. Additional guidance concerning the selection of ligands can be obtained from Michael Natan et al.'s Preparation and Characterization of Au Colloid Monolayers, *Anal. Chem.* 1995, 67, 735-743, which is incorporated herein by reference.

Sulfur-containing molecules (e.g., thiols, sulfides, thioesters, disulfides, sulfur-containing heterocycles, and mixtures thereof) comprise a particularly useful class of ligands. Thiols, for example, are a suitable type of sulfur-containing ligand for several reasons. Thiols have an affinity for gold, and gold, including gold particles, may be formed into electrodes or electrode patterns. Moreover, thiols are good ligands for stabilizing gold nanoparticles, and many sulfhydryl-based ligands are commercially available. The thiols form ligand-stabilized metal nanoparticles having a formula $M_x(SR)_n$ wherein M is a metal, R is an aliphatic group, typically an optionally substituted chain (such as an alkyl chain) or aromatic group, x is a number of metal atoms that provide metal nanoparticles having the characteristics described above, and n is the number of thiol ligands attached to the ligand-stabilized metal nanoparticles.

For incorporation into arrays, at least one nanoparticle ligand constitutes a linker molecule. A linker molecule is adapted to bind to the substrate and/or oxophilic metal deposited thereon, thereby linking the nanoparticle to the substrate. Linker functionalized nanoparticles include a wide variety of ligand-stabilized nanoparticles of the general formulas CORE-L-(S—X)$_n$ wherein L is the linker and X is a functional group or chemical moiety that serves to couple the nanoparticle to a substrate, and n is at least one.

For example, X may include without limitation phosphonic acid groups, carboxylic acid groups, sulfonic acid groups, peptide groups, amine groups, and ammonium groups. Other functional groups that may be part of X include aldehyde groups and amide groups. In one embodiment, linker functionalized nanoparticles are prepared from phosphine-stabilized nanoparticles of the formula CORE-$(PR_3)_m$, where the R groups are independently selected from the group consisting of aromatic, such as phenyl and aliphatic groups, such as alkyl, typically such alkyl groups have 20 or fewer carbons, for example, cyclohexyl, t-butyl or octyl, and n is at least one.

In one embodiment the linker molecule is bifunctional, having one functional group adapted to bind to a nanoparticle and a second functional group adapted to bind to the oxophilic metal. The first and second functional groups may be the same or different. One example of such bifunctional linker molecules have the formula

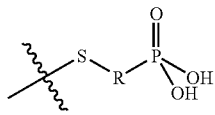

wherein R comprises an aliphatic group. In certain embodiments, R includes a lower alkyl group, and/or an aryl group, such as a phenyl or biphenyl moiety. In particular embodiments, R represents an alkylene group, optionally interrupted with one or more heteroatoms, such as oxygen or nitrogen. Examples of such alkylene groups interrupted with oxygen include polyethylene glycol (PEG) and/or polypropylene glycol (PPG) chains. As used herein, PEG and PPG refer to oligomeric groups having as few as two glycol subunits. Exemplary R groups include, without limitation, —$CH_2CH_2$—, —$CH_2CH_2OCH_2CH_2$— and —$CH_2CH_2OCH_2CH_2OCH_2CH_2$—.

C. General Method for Producing Ligand-Stabilized Metal Nanoparticles

The general approach to making ligand-stabilized, metal nanoparticles first comprises forming substantially or completely monodisperse metal nanoparticles having displaceable ligands. This can be accomplished by directly forming such metal nanoparticles having the appropriate ligands attached thereto, but is more likely accomplished by first forming such ligand-stabilized, metal nanoparticles, which act as precursors for subsequent ligand-exchange reactions with ligands that are more useful for coupling nanoparticles to substrates.

One example, without limitation, of a substantially monodisperse gold nanoparticle that has been produced, and which is useful for subsequent ligand-exchange reactions with the ligands listed above, is the 1.4 nm phosphine-stabilized gold particle described by Schmid, *Inorg. Syn.* 1990, 27, 214-218, which is incorporated herein by reference. Schmid's synthesis involves the reduction of AuCl[$PPh_3$]. Example 1 below also discusses the synthesis of 1.4 nm phosphine-stabilized gold particles. One advantage of this synthesis is the relatively small size distribution of nanoparticles produced by the method, e.g., 1.4±0.4 nm. The formula of such 1.4 nm gold nanoparticles has been shown to be $Au_{101}(PPh_3)_{21}Cl_3$ (See, Weare, W. W.; Reed, S. M.; Warner, M. G.; Hutchison, J. E. *J. Am. Chem. Soc.* 2000, 122, 12890-12891, which is incorporated herein by reference).

Once ligand-stabilized, substantially monodisperse metal nanoparticles are obtained, such nanoparticles can be used for subsequent ligand-exchange reactions, as long as the ligand-exchange reaction is readily facile and produces monodisperse metal nanoparticles. Previously, it was not appreciated that the ligand exchange chemistry phosphine-stabilized gold nanoparticles could yield nearly monodisperse 1.4 nm nanoparticles stabilized by ligands other than phosphines. In fact, some literature reports indicated that it was difficult, if not impossible, to form linked metal nanoparticles by ligand-exchange reactions. See, for example, Andres et al.'s Self-Assembly of a Two-Dimensional Superlattice of Molecularly Linked Metal Nanoparticles, *Science*, 1996, 273, 1690-1693.

To perform ligand-exchange reactions, a reaction mixture is formed comprising the metal nanoparticle having exchangeable ligands attached thereto and the ligands to be attached to the metal nanoparticle, such as thiols. A precipitate generally forms upon solvent removal, and this precipitate is then isolated by conventional techniques. See Example 3 for further details concerning the synthesis of ligand-stabilized 1.4-1.5 nm gold nanoparticles.

An example of a monodisperse gold nanoparticle is $Au_{11}$. Phosphine-stabilized undecagold particles are disclosed by Bartlett et al.'s Synthesis of Water-Soluble Undecagold Cluster Compounds of Potential Importance in Electron Microscopic and Other Studies of Biological Systems, *J. Am. Chem. Soc.* 1978, 100, 5085-5089, which is incorporated herein by reference. $Au_{11}(PPh_3)_8Cl_3$ may be prepared as described in Example 2. However, application of the present method for ligand exchange chemistry to smaller particles, e.g. phosphine-stabilized undecagold complexes was not a straightforward extension of the chemistry developed for the larger nanoparticles. The ligand exchange conditions used for the 1.4 nm gold particles fail when applied to $Au_{11}$ particles. However, conditions under which $Au_{11}(PPh_3)_8Cl_3$ undergoes controlled ligand exchange with a variety of thiols to produce both organic- and water-soluble nanoparticles are disclosed herein. Examples 4-6 demonstrate ligand exchange reactions of $Au_{11}(PPh_3)_8Cl_3$ with structurally diverse thiols. $Au_{11}(PPh_3)_8Cl_3$ is a particularly useful precursor for forming thiol-stabilized, $Au_{11}$ particles because it is a molecular species with a defined chemical composition and is thus monodisperse.

III. Production and Use of Gold Nanoparticles

Disclosed herein are embodiments of a method for producing gold nanoparticles that are substantially simpler and safer than the traditional route, which employs diborane gas (see Example 1, below). TEM, XPS and ligand (thiol) exchange reactions respectively reveal that the size, composition and reactivity of nanoparticles synthesized using this new method are comparable to those produced by the traditional route. Additionally, this simple route can produce large quantities of gold nanoparticles capped by tricyclohexylphosphine or trioctylphosphine, producing a novel class of trialkylphosphine-stabilized nanoparticles.

First described by Schmid in 1981, phosphine-stabilized gold nanoparticles, commonly referred to as "Au 55," paved the way for investigating the properties of metal nanoparticles. These nanoparticles have a diameter of about 1.4 nm, thus nanoparticles prepared by the Schmid protocol also are referred to herein as 1.4 nm nanoparticles. The small size and low dispersity of triphenylphosphine-passivated gold nanoparticles continues to make them important tools in nanoelectronics, biological tagging, and structural studies. Recently the ability to exchange thiol ligands onto triphenylphosphine-passivated nanoparticles was demonstrated, which enabled the coupling of small size and low dispersity with the stability of thiol-passivated gold. This facilitates applications that require both high stability and small core size, such as room temperature, Coulomb-blockade-based nanoelectronics. One embodiment of this method provides a convenient gram-scale synthesis of 1.4 nm triphenylphosphine-stabilized nanoparticles that are comparable in both size and reactivity to the traditional 1.4 nm nanoparticles prepared by the Schmid protocol. This route utilizes commercially available reagents and replaces a hazardous reducing agent. The generality of this synthetic method has been explored through the synthesis of previously unknown aliphatic, phosphine-stabilized gold nanoparticles, particularly trialkylphosphine-stabilized nanoparticles.

A working embodiment of the synthesis is illustrated by Scheme 1.

Scheme 1

$$HAuCl_4 + 3PPh_3 + NaBH_4 \xrightarrow{a} Au_{101}(PPh_3)_{12.5}Cl_3{}^b$$

With reference to Scheme 1, "a" refers to reaction conditions, including an organic-aqueous solvent system (e.g., toluene:water biphasic solvent system), a phase transfer catalyst, such as tetraoctylammonium bromide (see below), and a reaction time suitable to provide desired products (e.g., about 5 hours). Formula "b" is the empirical formula of the resulting product, which is based upon size and atomic composition measurements.

Phosphine-stabilized gold nanoparticles produced as described herein can be used in any applications in which traditionally synthesized gold nanoparticles are used.

In certain embodiments, gold nanoparticles can be used in combination with other labels, such as fluorescent or luminescent labels, which provide different methods of detection, or other specific binding molecules, such as a member of the biotin/(strept) avidin specific binding family (e.g., as described in Hacker et al. *Cell Vision* 1997, 4, 54-65.)

IV. EXAMPLES

The following examples are provided to illustrate certain particular embodiments of the disclosure. It should be understood that additional embodiments not limited to these particular features described are consistent with the following examples.

General Methods and Materials

Hafnium dichloride oxide octahydrate (Alfa Aesar; 99.998%), hafnium (IV) chloride (STREM; 99.9+%), n-octadecylphosphonic acid [$CH_3(CH_2)_{17}P(O)(OH)_2$] (Alfa Aesar), allyl mercaptan (Avocado Research Chemicals, Ltd.; 70%), zirconium dichloride oxide octahydrate (Alfa Aesar; 99.9%), Shipley 1818 Photoresist (Shipley Company, Marlborough, Mass.), Microposit 351 Developer (Shipley Company), and F-4 Photographic Fixer (Microchrome Technology, Inc., Reno, Nev.) were used as received. 2-Mercaptoethylphosphonic acid [$HS(CH_2)_2P(O)(OH)_2$] was synthesized as described in Example 11. Methyl alcohol (J. T. Baker; 100.0%) was distilled over magnesium. Deionized water (18.2 MΩ-cm) was purified with a Barnstead Nanopure Diamond system. Absolute ethyl alcohol (Aaper Alcohol and Chemical Company) was sparged with nitrogen for approximately 20 minutes prior to use.

Example 1

This example describes the synthesis of 1.4 nm phosphine-stabilized gold particles. AuCl(PPh$_3$) was reduced in benzene using diborane ($B_2H_6$), which was produced in situ by the reaction of sodium borohydride (NaBH$_4$) and borontrifluoride etherate [$BF_3.O(C_2H_5)$]. $Au_{55}(PPh_3)_{12}C_{16}$ was purified by dissolution in methylene chloride followed by filtration through Celite. Pentane was then added to the solution to precipitate a black solid. The mixture was filtered and the solid was dried under reduced pressure to provide 1.4 nm phosphine-stabilized gold particles in approximately 30% yield.

Example 2

This example describes the synthesis of $Au_{11}(PPh_3)_8Cl_3$, a triphenylphosphine-stabilized $Au_{11}$ nanoparticle. NaBH$_4$ (76 mg, 2.02 mmol) was slowly added to a mixture of AuCl(PPh$_3$) (1.00 g, 2.02 mmol) in absolute EtOH (55 mL) over 15 minutes. After stirring at room temperature for 2 hours, the mixture was poured into hexanes (1 L) and allowed to precipitate over approximately 20 hours. The resulting brown solid was collected and washed with hexanes (4×15 mL), $CH_2Cl_2$/hexanes (1:1 v/v 4×15 mL) and $CH_2Cl_2$/hexanes (3:1, 10 mL). The remaining solid was dissolved in $CH_2Cl_2$ (15 mL) and filtered a second time to remove a colorless, insoluble powder. Crystallization from $CH_2Cl_2$/hexanes gave $Au_{11}(PPh_3)_8Cl_3$ (140 mg, 18% yield) as deep red plates. The structure was confirmed by melting point, elemental analysis, X-ray photoelectron spectroscopy and $^1H$ NMR.

Example 3

This example describes the synthesis of 1.4 nm thiol-stabilized gold particles. Dichloromethane (~10 mL), 1.4 nm phosphine-stabilized gold particles (20.9 mg) and octadecylthiol (23.0 mg) were combined in a 25 mL round bottom. A black solution was produced, and this solution was stirred under nitrogen at room temperature for 36 hours. The solvent was removed under reduced pressure and acetone was added to suspend a black powder. The solid was isolated by vacuum filtration and washed with acetone (10×5 mL). After the final wash, the solid was redissolved in hot benzene. The benzene was removed under reduced pressure with gentle heating to yield a dark brown solid.

The solid material was then subjected to UV-VIS ($CH_2Cl_2$, 230-800 nm), $^1H$ NMR, $^{13}C$ NMR, X-ray photoelectron spectroscopy (XPS) and atomic force spectroscopy.

In the X-ray photoelectron spectroscopy (XPS) measurement, molecules are irradiated with high-energy photons of fixed energy. When the energy of the photons is greater than the ionization potential of an electron, the compound may eject the electron, and the kinetic energy of the electron is equal to the difference between the energy of the photons and the ionization potential. The photoelectron spectrum has sharp peaks at energies usually associated with ionization of electrons from particular orbitals. X-ray radiation generally is used to eject core electrons from materials being analyzed. Clifford E. Dykstra, *Quantum Chemistry & Molecular Spectroscopy*, pp. 296-295 (Prentice Hall, 1992).

Quantification of XPS spectra gave a gold-to-sulfur ratio of about 2.3:1.0 and shows a complete absence of phosphorus and chlorine. As is the case of the phosphine-stabilized nanoparticles, a broad doublet is observed for the Au 4f level. The binding energy of the Au 4f 7/2 level is about 84.0-84.2 eV versus that of adventitious carbon, 284.8 eV. This indicates absence of Au(I) and is similar to binding energies obtained for nanoparticles such as $Au_{55}(PPh_3)_{12}Cl_6$. The binding energy of the S 2p 3/2 peak ranges from 162.4 to 162.6 eV for the series of nanoparticles. These values are shifted to lower energy than those found for free thiols (163.3-163.9 eV) and are close to the values reported for thiolates bound to bulk gold (162.0-162.4 eV). $^1$H and $^{13}$C NMR unambiguously rules out the possibility that unattached thiols may be present in the sample.

Thermal gravimetric analysis confirmed the Au:S ratio obtained from XPS. On heating to 600° C., ODT-stabilized nanoparticles display a 40% mass loss, corresponding to 26 ODT ligands on an assumed 55-atom gold nanoparticle. This ratio alludes to the retention of a small nanoparticle size. A sample of the larger hexadecanethiol-stabilized gold nanoparticle has been shown to give a 33.5% mass loss, corresponding to from about 95 to about 126 ligands per nanoparticle (diameter=2.4 nm).

Optical spectra of gold colloids and nanoparticles exhibit a size-dependent, surface plasmon resonance band at about 520 nm. In absorption spectra of ligand-exchanged nanoparticles produced as stated in this example, the interband transition typically observed for small nanoparticles, including $Au_{55}(PPh_3)_{12}Cl_6$, was observed. Little or no plasmon resonance was observed, consistent with a nanoparticle size of about 1.7 nm or less. For the ODT-passivated nanoparticle, no plasmon resonance was observed.

Quantitative size information can be obtained using transmission electron microscopy (TEM). The core size obtained from TEM images of the ODT-stabilized nanoparticle was found to be 1.7±0.5 nm and agrees with the size obtained from atomic force microscope images.

Atomic force microscopy (AFM) also was performed on the $Au_{55}(SC_{18}H_{37})_{26}$ produced according to this example. The analysis produced a topographical representation of the metal complex. AFM probes the surface of a sample with a sharp tip located at the free end of a cantilever. Forces between the tip and the sample surface cause the cantilever to bend or deflect. The measured cantilever deflections allow a computer to generate a map of surface topography. Rebecca Howland et al. *A Practical Guide to Scanning Probe Microscopy*, p. 5, (Park Scientific Instruments, 1993). The AFM data for particles produced according to this example showed heights of 1.5 nm for single nanoparticles and aggregates subjected to high force. This corresponds to the size of the gold core nanoparticles. This helped establish that the gold nanoparticles of this example were close to the correct size for forming useful devices. In a manner similar to that described above for Example 2, thiol stabilized structures also have been made using 1-propanethiol.

Example 4

This example describes the preparation of an organic-soluble, octadecane thiol-stabilized $Au_{11}$ particles from monodisperse $Au_{11}(PPh_3)_8Cl_3$ via ligand exchange. A mixture of $Au_{11}(PPh_3)_8Cl_3$, prepared according to the procedure of Example 2, (10 mg, 2.3 µmol) and octadecanethiol (13 mg, 45 µmol) dissolved in $CHCl_3$ (30 mL) was stirred for 24 hours at 55° C. Volatiles were removed and the crude solid product was dissolved in i-PrOH and filtered to remove insoluble Au(I) salts. The filtrate was purified via gel filtration over Sephadex LH-20 using i-PrOH as the eluent. The purified octadecanethiol-stabilized particles yielded satisfactory $^1$H NMR and $^{13}$C NMR. Well-defined optical absorptions in the visible spectrum are distinguishable from the spectra obtained for the larger 1.5 nm core particles by inspection.

Example 5

This example describes the preparation of a water-soluble, (N,N-dimethylamino) ethanethiol-stabilized $Au_{11}$ particle. A mixture of (N,N-dimethylamino) ethanethiol hydrochloride (12 mg, 85 µmol) in degassed $H_2O$ (30 mL) and $Au_{11}(PPh_3)_8Cl_3$ (20 mg, 4.6 µmol) in degassed $CHCl_3$ (30 mL) was stirred vigorously for 9 hours at 55° C. (until all colored material was transferred into the aqueous layer). The layers were separated and the aqueous layer washed with $CH_2Cl_2$ (3×15 mL). Volatiles were removed and the crude solid product was dissolved in EtOH (3 mL) and precipitated with hexanes. The precipitate was collected on a frit and washed with hexanes (30 mL) and $CHCl_3$ (30 mL). The washed material yielded analytical data ($^1$H NMR, TEM, XPS) consistent with (N,N-dimethylamino) ethanethiol-stabilized $Au_{11}$ nanoparticles of an average core size of 0.9±0.2 nm.

Example 6

This example concerns the preparation of a water-soluble, sodium 2-mercaptoethanesulfonate-stabilized $Au_{11}$ particle. A mixture of $Au_{11}(PPh_3)_8Cl_3$ (29 mg, 6.7 µmol) in $CHCl_3$ (20 mL) and sodium-2-mercaptoethanesulfonate (24 mg, 146 µmol) in $H_2O$ was stirred vigorously for 1.5 hours at 55° C., until all colored material was transferred into the aqueous layer. The layers were separated and the aqueous layer was extracted with $CH_2Cl_2$ (3×20 mL). After removal of the water, the crude product was suspended in methanol, transferred to a frit and washed with methanol (3×20 mL). The resulting material (25 mg, 5.8 µmol) and additional sodium 2-mercaptoethanesulfonate (5 mg, 30 µmol) in $H_2O$/THF (1:1, 40 mL) was stirred vigorously for 6 h at 50° C. The mixture was washed with $CHCl_3$ (3×20 mL) to remove THF. After the water was removed in vacuo the crude material was suspended in methanol (30 mL), transferred to a frit and washed with methanol (3×20 mL) to remove excess ligand. $^1$H NMR, XPS analysis, and TEM micrographs confirmed the desired structure.

Example 7

This example describes the synthesis of 4-mercaptobiphenyl-stabilized 1.4 nm gold nanoparticles. Dichloromethane (~10 mL), 1.4 nm triphenylphosphine-stabilized gold nanoparticles (prepared according to the procedure of Example 1) (25.2 mg) and 4-mercaptobiphenyl (9.60 mg) were combined in a 25 mL round bottom. The resulting black solution was stirred under nitrogen at room temperature for 36 hours. The solvent was removed under reduced pressure and replaced with acetone. This resulted in the formation of a black powder suspension. The solid was isolated by vacuum filtration and washed with acetone (6×5 mL). The solvent was then removed under reduced pressure to yield 16.8 mg of a dark brown solid.

The solid material was subjected to UV-Vis ($CH_2Cl_2$, 230-800 nm), $^1$H NMR, $^{13}$C NMR, X-ray photoelectron spectroscopy (XPS) and atomic force spectroscopy as in Example 2. This data confirmed the structure and purity of the metal complex, and further showed complete ligand exchange. For example, quantification of the XPS data for material prepared according to this example showed that Au 4f comprised about 71.02% and S 2p constituted about 28.98%, which suggests a formula of $Au_{55}(S\text{-biphenyl})_{25}$.

AFM analysis showed isolated metal nanoparticles measuring about 2.5 nm across, which correlates to the expected size of the gold core with a slightly extended sphere.

Thiol-stabilized nanoparticles produced as described above display remarkable stability relative to 1.4 nm phosphine-stabilized gold nanoparticles, which decomposes in solution at room temperature to give bulk gold and AuCl

[PPh$_3$]. No decomposition for the thiol-stabilized nanoparticles was observed, despite the fact that some samples were deliberately stored in solution for weeks. In other tests, the mercaptobiphenyl and octadecylthiol-stabilized nanoparticles (in the absence of free thiol) were heated to 75° C. for periods of more than 9 hours in dilute 1,2-dichloroethane solution with no resultant degradation. Under identical conditions, 1.4 nm phosphine-stabilized gold nanoparticles decompose to Au(O) and AuCl[PPh$_3$] within 2 hours.

Example 8

This example describes the electron transfer properties of organometallic structures formed by electron-beam irradiation of 1.4 nm phosphine-stabilized gold nanoparticles. This compound was produced as stated above in Example 1. A solution of the gold nanoparticle was made by dissolving 22 mg of the solid in 0.25 mL of CH$_2$Cl$_2$ and 0.25 mL of 1,2-dichloroethane. A supernatant solution was spin coated onto a Si$_3$N$_4$ coated Si wafer at 1,500 rpm for 25 seconds immediately after preparation. The film was patterned by exposure to a 40 kV electron beam at a line dosage of 100 nC/cm. The areas of the film exposed to the electron beam adhered to the surface and a CH$_2$Cl$_2$ rinse removed the excess film. This procedure produced well-defined structures. These structures appeared to be smooth and continuous under SEM inspection. Attempts were made to pattern the material using 254 nm UV lithography, but it was found to be insensitive to this wavelength. The defined structures had dimensions as small as 0.1 μm and AFM inspection measured the film thickness to be 50 nm.

The organometallic samples were spin-coated with PMMA that was electron-beam exposed and developed to define contact regions. Contacts were fabricated using thermal evaporation of 100 nm of gold and conventional liftoff procedures.

DC current-voltage (I-V) measurements of several samples were taken. A shielded chamber, submerged in an oil bath, contained the sample mounted on a clean teflon stage. Rigid triaxial connections were used to connect the sample to a constant DC voltage source and electrometer. The oil bath temperature was controlled from 195 to 350K. Thermal equilibrium was achieved with a 10 Torr partial pressure of He in the chamber. Before electrical measurements the chamber was evacuated to a pressure ~$10^{-5}$ Torr. The data showed little temperature drift over a typical four hour measurement sweep. The intrinsic leakage current of the system was measured using a control sample having the same substrate and contact pad arrangement as the actual samples, but did not have the organometallic between the pads. At room temperature, the leakage current was almost linearly dependent on bias over the range −100 to 100V, and had a maximum value ≦100 fA. While the ultimate resolution of the current measurement was 10 fA, the leakage current set the minimum resolved conductance ~$10^{-15}\Omega^{-1}$. Constant amplitude RF signals with frequencies, f, from 0.1 to 5 MHz, were applied to the samples through a dipole antenna at 195K. No attempt was made to optimize the coupling between the RF signal and the sample.

For one sample, as the temperature was reduced, the low voltage portion of the curve flattened out and the current became indistinguishable from the leakage current. Above an applied voltage magnitude of 6.7±0.6 V, the current increased abruptly. This establishes that substantially monodisperse gold nanoparticles can produce devices that operate on the basis of the Coulomb blockade effect.

Application of the RF signal introduced steps in the I-V characteristic, establishing that an applied external varying signal (the frequency of which is provided by the X axis) actually controls the rate at which electrons move through the metal nanoparticles. The current at which these steps occurred was found to be proportional to the applied signal frequency. A least squares analysis of the linear current-frequency relationship for the highest current step shown gives a slope of 1.59±0.04×$10^{-19}$ C.

The introduction of plateaus in the patterned sample I-V characteristics is similar to the RF response reported in other Coulomb blockade systems. This effect has been attributed to phase locking of single-electron tunneling events by the external RF signal. When the nth harmonic of the applied frequency corresponds to the mth harmonic of the frequency of tunneling in the system, mIIe, the current becomes locked to a value I=(n/m)ef. The results obtained suggest that correlated tunneling is present in the samples.

The patterned samples had stable I-V characteristics with time and temperature. Furthermore, as the temperature was raised above about 250K the I-V characteristics developed almost linear behavior up to $V_T$. The conductance below $V_T$ was activated, with activation energies $E_A$ in the range of from about 30 to about 70 meV. The charging energy can be estimated from the activation energy. Assuming current suppression requires $E_c$≧10kT, the sample with the largest activation energy should develop a Coulomb gap below ~300 K. This value is within a factor of 2 of the measured temperature at which clear blockade behavior occurs in the patterned samples. Given the accuracy to which $E_c$ is known, the temperature dependence of the conductance within the Coulomb gap is consistent with the observation of blockade behavior. Using this value of $E_c$, the effective capacitance of a metal core in the patterned array is $3\times10^{-19}$F<C<$7\times10^{-19}$F. These values are close, but larger than the classical geometric capacitance of an isolated 1.4 nm gold nanoparticle, where C=4π∈∈$_0$r~$2\times10^{-19}$F, and where the dielectric constant, ∈, of the surrounding ligand shell is expected to be ~3. The agreement between the two estimates indicates that the current suppression in the metal nanoparticle arrays is due to charging of individual 1.4 nm gold nanoparticles.

The non-linear I-V characteristic is similar to that of either a forward biased diode or one-/two-dimensional arrays of ultra small metal islands or tunnel junctions. However, the dependence of the I-V characteristic on the applied RF signal is not consistent with straightforward diode behavior. Therefore, the data has been analyzed in the context of an array of ultra small metal islands.

Several reports have discussed the transport in ordered arrays of tunnel junctions that have tunneling resistances greater than the quantum resistance h/e$^2$ and a charging energy significantly above the thermal energy. In this case Coulomb blockade effects introduce a threshold voltage below which current through the array is suppressed. As the applied voltage is increased well beyond threshold, the current-voltage characteristic approaches a linear asymptote with a slope related to the tunnel resistance. With the same temperature and tunnel resistance constraints, Middleton and Wingreen have discussed one- and two-dimensional arrays of maximally disordered normal metal islands where disorder is introduced as random offset charges on each dot. These authors predict current suppression below a threshold voltage and high bias current I~$(V/V_T-1)^\gamma$. Here, the threshold voltage $V_T$ scales with the number of junctions N along the current direction. Analytically γ=1 for one-dimensional systems and 5/3 for infinite two-dimensional systems. Numerical simulations of a finite two-dimensional array gave γ=2.0±0.2.

While no effort was made to order samples, data were analyzed using both the ordered and the disordered models. The only consistent analysis was found to be given by the disordered model. In particular, the high bias data did not have the linear asymptote predicted for an ordered system, but did scale as expected for a disordered system. A two-dimensional array was produced, such that charge propagates through the sample tested along plural parallel paths. Such an arrangement is useful for developing memory storage devices. The exponent $\gamma \sim 1.6$ is closest to the analytical prediction for an infinite, disordered two-dimensional array. From the analysis the magnitude of $V_T \sim 6 \pm 1$ V agrees with that estimated directly from the I-V data.

The introduction of steps in the I-V characteristics by a RF field is similar to the RF response reported in other systems. This effect has been attributed to phase locking of single-electron tunneling events by the external RF signal. If the applied frequency corresponds to a rational fraction multiple of the frequency of tunneling in the system, I/e, then the current is locked to a value $I=(n/m)ef$, where n and m are integers. Therefore, the linear relationships between f and I suggest that correlated tunneling is present in the samples. The lowest slope observed is best described with $n/m=\frac{1}{5}$. For frequencies up to 3 MHz, the current resolution is insufficient to distinguish between the ⅕ and ¼ harmonics. However, at higher frequencies where it should have been possible to distinguish between ⅕ and ¼, the ¼ step was not observed.

At temperatures above about 250K, the I-V characteristic was almost linear up to $V_T$. In this regime the conductance was activated, with activation energies $E_A$ in the range 30 to 70 meV for the samples studied. Similar activated behavior has been reported for tunnel junction systems. It was argued that for an infinite 2D array the charging energy for one island $E_C \approx 4E_A$. Applying this argument to the present system, and assuming current suppression requires $E_C \geqq 10$ kT, the sample with the largest activation energy should develop a Coulomb gap below about 300 K. This estimate is within a factor of two of the measured temperature at which clear blockage behavior is seen. Thus, the temperature dependence of the observed current within the Coulomb gap is consistent with the observation of blockade behavior. From the threshold voltage, $V_T = \alpha Ne/C$, and this estimate of $E_C$, $\alpha N$ is approximately 10.

The energy $E_C$ also can be estimated if the capacitance of an island is known. The capacitance of an isolated 1.4 nm gold nanoparticles nanoparticle is $C=4\pi \in \in_o \tau$, where $\tau$ is the radius of the nanoparticle and $\in$ is the dielectric constant of the surrounding medium. The radius of an 1.4 nm gold nanoparticles nanoparticle is 0.7 nm and the ligand shell is expected to have $\in \in 3$, which $C \approx 2 \times 10^{-19}$F. The Coulomb charging energy, $E_C = e^2/2C \approx 340$ meV, is within twenty percent of the maximum value of $4E_A$ found from the activation data. This result suggests that the current suppression is due to charging of individual 1.4 nm gold nanoparticles.

Given the constraint that steps in the I-V characteristics are only found when $f<0.1/(R_T C)$, the fact that steps are seen up to f=5 MHz gives the upper limit $R_T<1\times10^{11} \Omega$. The differential resistance obtained from the I-V characteristic well above threshold is anticipated to be $R_{diff} \approx (N/M)R_T$, where M is the number of parallel channels. This estimate yields N/M 30. From the sample dimensions and the size of an individual nanoparticle, a close packed array would have $N/M \geqq 5$. This disparity between the expected and experimentally derived values of the N/M suggests that the full width of the sample is not involved in transport. One explanation for the discrepancy in N/M may be that many of the gold cores coalesce during sample fabrication so that transport is dominated by individual nanoparticles between larger regions of gold.

Example 9

This example describes a method for making phosphine-stabilized gold nanoparticles, particularly 1.4 nm (±0.5 nm) phosphine-stabilized gold nanoparticles. Traditional methods for making such molecules are known, and are, for instance, described by G. Schmid (*Inorg. Syn.* 1990, 27, 214-218) and in Example 1.

HAuCl$_4$+3PPh$_3$+NaBH$_4$→Au$_{101}$(PPh$_3$)$_{12.5}$Cl$_3^b$    Scheme 1

Scheme 1 (above) illustrates a convenient one-pot, biphasic reaction in which the nanoparticles can be synthesized and purified in less than a day from commercially available materials. Hydrogen tetrachloroaurate trihydrate (1.11 g, 3.27 mmol) and tetraoctyl-ammonium bromide (1.8 g, 3.3 mmol) were dissolved in a nitrogen-sparged water/toluene mixture (100 mL each). Triphenylphosphine (2.88 g, 11.0 mmol) was added, the solution stirred for five minutes until the gold color disappeared, and aqueous sodium borohydride (2.0 g, 41.0 mmol, dissolved in 5 mL water immediately prior to use) was rapidly added resulting in a dark purple color (this addition results in vigorous bubbling and should be performed cautiously). The mixture was stirred for three hours under nitrogen, the toluene layer was washed with water (5×100 mL) to remove the tetraoctylammonium bromide and borate salts and the solvent removed in vacuo to yield 1.3 g of crude product.

To effect further purification, the resulting solid was suspended in hexanes, filtered on a glass frit, and washed with hexanes (300 mL) to remove excess triphenylphosphine. Washing with a 50:50 mixture of methanol and water (300 mL) removed triphenylphosphine oxide. Each of these washes was monitored by TLC and the identity of the collected material was confirmed by $^1$H and $^{31}$P NMR. Pure samples were obtained by precipitation from chloroform by the slow addition of pentane (to remove gold salts, as monitored by UV-Vis and NMR). After purification, this procedure yielded 644 mg of purified nanoparticle product from 1.35 g of hydrogen tetrachloroaurate (yield>90%). In contrast, the traditional synthesis yields about 300 mg of purified nanoparticle product per 2 g hydrogen tetrachloroaurate (29% yield).

For comparison of these nanoparticles to the products of the traditional synthesis the newly synthesized nanoparticles were analyzed to determine size, atomic composition, and reactivity as described below. The small size of the nanoparticles, which allows for examination of Coulomb blockade phenomena at room temperature, is a consideration for evaluating the effectiveness of the synthesis.

Direct evidence of nanoparticle size and dispersity is provided by transmission electron microscopy (TEM). TEM was performed on a Philips CM-12 microscope operating at a 100 kV accelerating voltage. Samples were prepared by drop casting dilute methylene chloride solutions onto 400-mesh nickel grids coated with carbon. Images were recorded as photographic negatives, scanned, and processed using NIH image software. A total of 1628 particles were examined from two separate synthetic runs, for the triphenylphosphine nanoparticles. Background noise and agglomerated nanoparticles were removed from the measurements by removing core sizes of <0.5 nm and >3 nm from the analysis. A representative TEM showed nearly monodisperse triphenylphosphine nanoparticles with a size of 1.4 nm±0.5 nm.

UV/Vis spectroscopy, a technique that is representative of the bulk material, was used to confirm TEM size determinations. UV-visible spectroscopy was performed on a Hewlett-Packard HP 8453 diode array instrument with a fixed slit width of 1 nm using 1 cm quartz cuvettes. The absence of a significant surface plasmon resonance at ~520 nm indicates gold nanoparticles that are <2 nm diameter. UV/Vis spectra of newly synthesized nanoparticles are dominated by an interband transition, with no significant plasmon resonance at 520 nm. This indicates that there is no substantial population of nanoparticles greater than 2 nm in size.

Atomic composition of the nanoparticles was determined using the complementary techniques of x-ray photoelectron spectroscopy (XPS) and thermogravimetric analysis (TGA) allowing further comparison to traditionally prepared nanoparticles. TGA was performed under a nitrogen flow with a scan rate of 5° C. per minute. XPS was performed on a Kratos Hsi operating at a base pressure of $10^{-8}$ ton. Samples were prepared by drop-casting a dilute organic solution of the nanoparticles onto a clean glass slide. Charge neutralization was used to reduce surface charging effects. Multiplexes of carbon, sulfur, and phosphorus were obtained by 30 scans each. Binding energies are referenced to adventitious carbon at 284.4 eV. Data were recorded with a pass energy of 20 eV. XPS spectra provides an average composition of 71% gold, 26% carbon, 2.6% phosphine, and 0.7% chlorine, corresponding to molar ratios of 18 Au: 108 C:4.3 P:1 Cl. TGA indicates a mass ratio of 71% gold to 29% ligand, independently confirming the ligand-to-ratio determined by XPS. For direct comparison with the nanoparticles made by traditional methods, an average empirical formula was generated by assuming a core size of 55 gold atoms. Based on the average particle size, the particles produced by the method were identified as $Au_{101}(PPh_3)_{12.5}Cl_3$, in comparison with the $Au_{55}(PPh_3)_{12}Cl_6$ reported by Schmid. While the gold-to-phosphorus ratio matches that of the Schmid nanoparticles, the phosphorus-to-chlorine ratio of 4:1 is double that of the Schmid nanoparticles (2:1).

The reactivity of the nanoparticles to thiol ligand exchange further confirms their similarities to traditional triphenylphosphine-stabilized nanoparticles. Using previously reported methods, ligands including a number of straight-chain alkanethiol, such as straight-chain alkylthiols having 2-20 carbon chains, and charged ω-functionalized alkanethiol, such as ω-carboxyalkanethiols, have been exchanged onto these nanoparticles. In each thiol-for-phosphine ligand exchange reaction, there is little change in the surface plasmon resonance of the UV/Vis spectra, indicating negligible size changes during the thiol-for-phosphine ligand exchange. Thus, the newly synthesized nanoparticles are similar in size, atomic composition, and reactivity to the Schmid preparation.

Disclosed embodiments of the method have enabled the facile formation of various nanoparticles substituted with phosphine ligands that have previously not been employed. Substitution of $PR_3$ for $PPh_3$, and slight modification of the work-up, allows for isolation of trialkylphosphine-stabilized nanoparticles in good yield. Trioctylphosphine- and tricyclohexylphosphine-stabilized gold nanoparticles have been successfully synthesized, which appear to be substantially larger by UV/Vis spectroscopy. This approach apparently is the first reported synthesis of trialkylphosphine-stabilized gold nanoparticles.

This synthesis allows for the expansion of phosphine-stabilized nanoparticle materials. Large amounts of nanoparticle material can be made in a single step using borohydride in place of diborane. Second, this synthesis allows for flexibility in the choice of phosphine ligand that was previously unknown. Variation of ligand-to-gold ratios using the disclosed embodiments can be used to achieve unprecedented size control of phosphine-stabilized gold nanoparticles.

Example 10

This example describes a method for determining the size of the nanoparticles made using a process similar to that described in Example 9. Controlling the rate at which the reducing agent, such as sodium borohydride, is added to the reaction mixture can be used to make nanoparticles materials having desired core diameters, such as a gold core diameter ($d_{core}$<2 nm). The synthesis is the same in every respect as that stated in Example 9 except for the addition rate of the reducing agent ($NaBH_4$). In Example 9, $NaBH_4$ was added rapidly. In this preparation the same quantity of reducing agent was added slowly (over a period of 10 minutes) from a dropping funnel fitted with a ground glass joint and Teflon stopcock. The resultant nanoparticles were shown by UV-visible spectroscopy to have an average diameter of larger than 2 nm.

Example 11

This example describes the synthesis of (2-mercaptoethyl)-phosphonic acid. Synthesis of (2-mercaptoethyl)-phosphonic acid: Triphenylmethanethiol (8.56 g, 30.8 mmol) was added to NaH (0.8 g, 30 mmol) in 250 mL dry THF, yielding a yellow solution. (2-bromoethyl)-phosphonic acid diethyl ester (5 mL, 38.1 mmol) was added and the solution stirred for 1 hour. The excess NaH was quenched with 25 mL of water. The resulting mixture was evaporated to ca. 20 mL, dissolved in 100 mL water and extracted with 3×150 mL $CH_2Cl_2$. The organic layer was concentrated by rotary evaporation and dried in vacuo for 2 hours. Upon trituration with 20 mL of diethyl ether, a white solid formed. The mixture was cooled to −78° C. and filtered. After rinsing with 25 mL of cold (−78° C.) diethyl ether, the white product, (2-tritylsulfanylethyl)-phosphonic acid diethyl ester, was dried in vacuo (10.6 g, 86% yield): $^1$H NMR (300 MHz, $CD_2Cl_2$) δ 7.4 (m, 15H), 3.95 (m, 4H), 2.65 (m, 2H), 2.35 (m, 2H), 1.2 (t, 6H).

To remove the trityl protecting group, the product was dissolved in 50 mL of trifluoroacetic acid (TFA). Triethylsilane was added dropwise to the rapidly stirring solution until the yellow color was gone and a white solid precipitated. Once the precipitate was removed via vacuum filtration, the TFA was evaporated to yield a colorless oil. The oil was transferred to a flask equipped with a Dean Stark trap and condenser and hydrolyzed in 150 mL of refluxing 5 M HCl for 48 hours. The aqueous layer was washed with 2×100 mL of chloroform and was concentrated by rotary evaporation and dried in vacuo to yield 2-mercaptoethyl phosphonic acid, an off-white solid (2.9 g, 73% overall yield): $^1$H NMR (300 MHz, $D_2O$) δ 2.75 (m, 2H), 2.08 (m, 2H).

Example 12

This example describes patterning of silicon oxide surfaces and forming nanoparticle arrays on the patterned surface. One embodiment of this approach is illustrated in FIGS. 14-17b. 1.5 nm triphenylphosphine (TPP) stabilized particles (Hutchison, J. E.; Foster, E. W.; Warner, M. G.; Reed, S. M.; Weare, W. W. In *Inorg. Syn.*; Buhro, W., Yu, H., Eds., 2004; Vol. 34, pp 228, which is incorporated herein by reference) were dissolved in dichloromethane and stirred with one mass equivalent of (2-mercaptoethyl)-phosphonic acid dissolved in water. When the organic layer was nearly colorless (ca. 24 hours), the aqueous layer was separated and washed with 2×100 mL dichloromethane. Any excess dichloromethane was removed by rotary evaporation at room temperature. The phosphonic acid particles were then purified by diafiltration (10 kD membrane, Spectrum Laboratories, Inc.). Nanoparticles were considered pure when no free ligand was evident by $^1$H NMR. Following diafiltration, the aqueous nanoparticle solution was passed through a 0.4 μm syringe filter and lyophilized to dryness. To make up the soaking solutions for nanoparticle deposition, the nanoparticles must be dissolved in pure water first and diluted with methanol to the desired concentration (2.5 mg/mL; 3:1 methanol:water).

Silicon substrates were cleaned prior to use for 10 minutes in piranha (5:1, $H_2SO_4$:$H_2O_2$) at 90° C., followed by 10 minutes in 200:4:1 $H_2O$:$H_2O_2$:$NH_4OH_2$. For EPMA/SEM studies, Shipley 1818 photoresist was deposited by spin-coating at 5000 rpm. A photomask was used to expose 300 μm squares with UV light at 13.4 mW/s for 11 seconds. The resist was developed in Shipley Microposit 351 for 1 minute and rinsed with nanopure water. The film was then treated with oxygen plasma with 30 sccm of oxygen at 150 W RF power for 8 seconds to remove photoresist residue, and rinsed with water. The exposed silicon was functionalized with $Hf^{+4}$ in an aqueous 5 mM solution of $HfOCl_2$ for 3 days at 50° C. The substrates were sonicated in acetone to dissolve the photoresist, and rinsed with copious amounts of water and acetone. The substrates were then soaked in a solution of phosphonic acid-functionalized nanoparticles for five days at room temperature. Substrates for TEM were prepared as above excluding the photolithography steps. The samples were polished to electron transparency by mounting on a tripod polisher with Crystal Bond and thinned with diamond lapping paper.

TEM was performed at 120 KV accelerating voltage on a Philips CM-12 microscope. EPMA data collection was performed using a Cameca SX-50. Intensities were measured on 4 wavelength dispersive spectrometers (WDS) using gas flow proportional detectors with P-10 (90% Ar, 10% methane) gas. Background subtraction was accomplished using off-peak and/or mean atomic number (MAN) calibration. (Donovan, J. J.; Tingle, T. N. J. *Microsc. Soc. Am.* 1996, 2, 1.) Quantitative interference corrections were performed according to the method developed by Donovan, et al. (Donovan, J. J.; Snyder, D. A.; Rivers, M. L. *Microbeam Anal* 1993, 2, 23.).

As described above, the silicon substrates were cleaned prior to use. In one embodiment the surface is treated prior to use to increase surface silanol concentration. Increased surface silanol concentration allows the coupling of a greater concentration of hafnium. The density of hafnium deposition is monitored by XPS measurement of Hf:Si ratio. A higher Hf 4f:Si 2p ratio indicates a surface silanol concentration.

In one embodiment, a silicon wafer is subjected to an oxygen plasma treatment followed by a wet chemical treatment to remove organic contaminants from the surface. After this treatment the wafers are ready for treatment with $HfOCl_2$ and subsequent processing as described above. In certain examples the oxygen plasma treatment is at about 150 mBar to about 500 mBar at 400 W for 120 seconds. In one embodiment the wet chemical treatment involves holding wafers in a solution of 200 parts $H_2O$ to 4 parts 30% $H_2O_2$ to 1 part 25% $NH_4OH$ 60° C. for 24 hours following the plasma treatment.

Example 13

This example describes the functionalization of a gold substrate. In this assembly strategy, gold substrates are first ozone treated and then soaked in a 5 mM solution of $HfCl_4$ in methanol. Upon removal from the hafnium solution, the substrates are rinsed with nanopure water for 15 minutes and then soaked in a 1 mM ethanolic solution of octadecylphosphonic acid (ODPA). Control experiments were also performed where the gold substrate was immediately placed in the ODPA soaking solution after ozone treatment. After soaking for at least 24 hours, the resulting substrates were characterized with contact angle goniometry, PM-IRRAS, and x-ray photoelectron spectroscopy (XPS).

ODPA monolayers formed directly on gold yielded a static contact angle of 82±3°, whereas the contact angle measured for ODPA monolayers formed on gold with the hafnium linker was 105±2°. This measurement is in good agreement with the static contact angle measured for ODPA monolayers on other substrates, including $TiO_2$ (104±2°).

Figure 13:
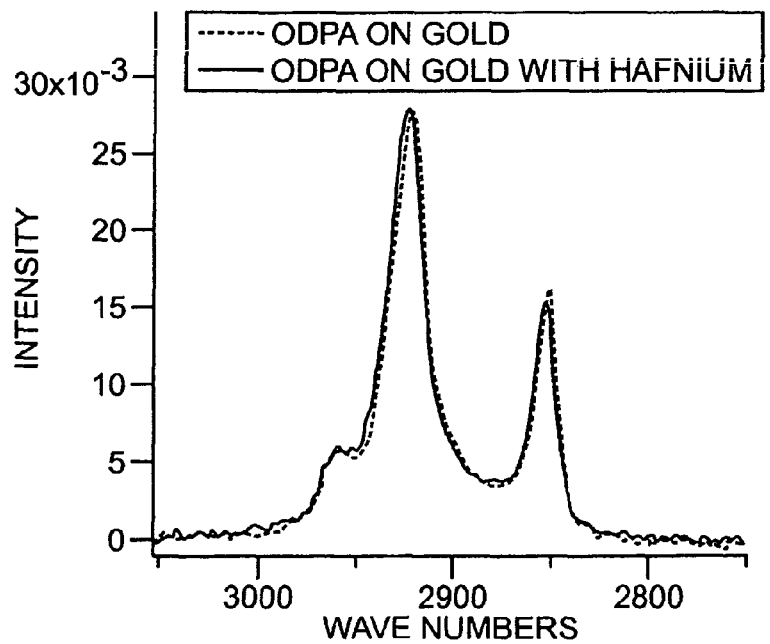
FIG. 13 includes PM-IRRAS spectra for octadecylphosphonic acid monolayers formed directly on gold (dashed line) and on gold modified with a hafnium linker (solid line).
Figure 14:
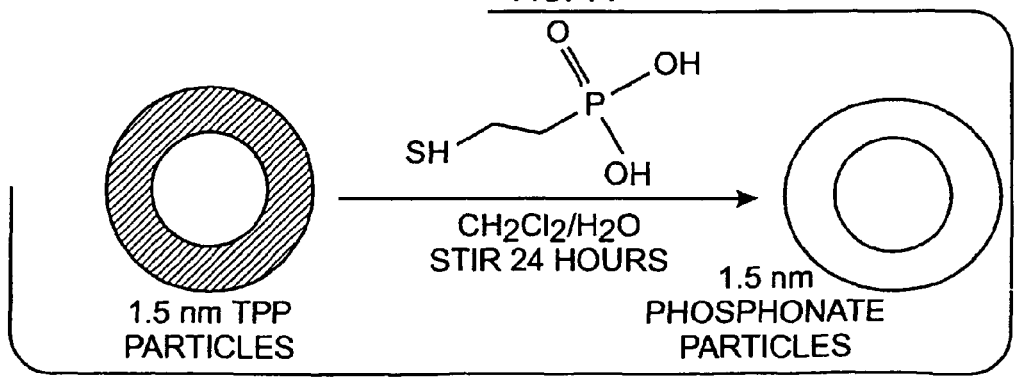
FIG. 14 illustrates gold nanoparticle synthesis.
Figure 15:
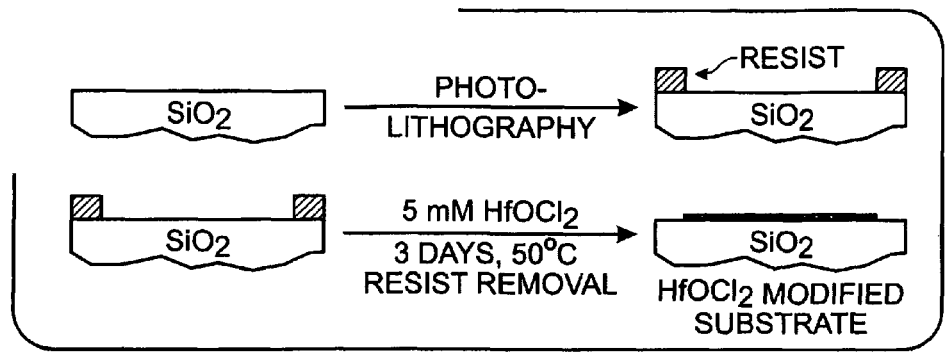
FIGS. 15 and 16 illustrate processing steps for surface functionalization and fabrication of gold nanoparticle patterned substrates.
Figure 16:
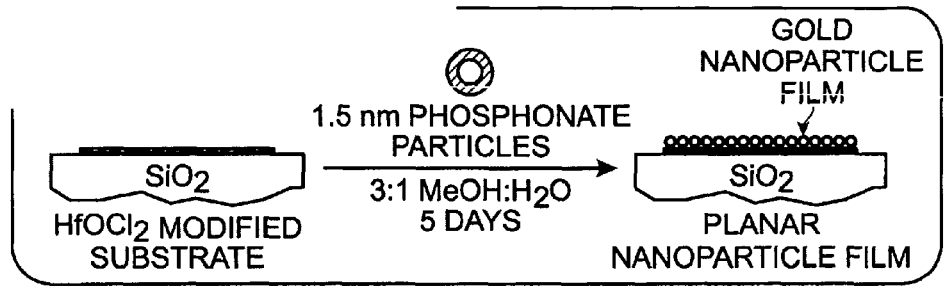

With reference to FIG. 13, PM-IRRAS data shows two major peaks for ODPA assemblies deposited directly onto gold as well as monolayers formed on gold with a hafnium linker. The two peaks at 2922 $cm^{-1}$ and 2851 $cm^{-1}$ correspond to the $CH_2$ (asym) and $CH_2$ (sym) peaks, respectively. The shoulder of the $CH_2$ (asym) peak at 2959 $cm^{-1}$ corresponds to the $CH_3$ (asym) peak. These peak positions are in good agreement with the IR spectra observed for ODPA monolayers on other substrates. The fact that the spectra for ODPA on gold are within experimental uncertainty indicates that the presence (or absence) of the hafnium linker has no impact on the organization/orientation of the resulting ODPA monolayer.

The XPS data for ODPA monolayers formed on gold with and without the hafnium linker provide atomic concentration quantification (summarized in the table below). No phosphorus is observed for ODPA assemblies formed on gold without a hafnium linker present, indicating that any ODPA present on these substrates is below the detection limit of the instrument. The XPS data for ODPA assemblies formed on hafnium modified gold show the presence of hafnium, phosphorus, oxygen and a significant amount of carbon. The gold peak is also significantly attenuated. These data indicate that an ODPA monolayer has formed on the hafnium modified gold.

Atomic quantification of XPS data for ODPA monolayers formed on gold with and without a hafnium linker:

| Monolayer | Au (4f) | P (2p) | C (1s) | O (1s) | Hf (4f) |
|---|---|---|---|---|---|
| ODPA on gold | 59 | 0 | 33 | 5 | — |
| ODPA on hafnium modified gold | 22 | 6 | 58 | 10 | 2 |

The contact angle, PM-IRRAS, and XPS data all indicate the presence of a high quality ODPA monolayer on hafnium modified gold. The contact angle and XPS data for the ODPA deposited on bare gold suggests that no monolayer is formed, however the PM-IRRAS data indicate the presence of a monolayer structure. Taken together, these data indicate that this example demonstrates that high quality phosphonate monolayers can be formed on gold using a hafnium linker molecule.

Example 14

This example describes an embodiment of a method wherein the bifunctional molecule 2-mercaptoethylphosphonic acid (2-MEPA) is assembled on a gold substrate that has been patterned with hafnium. Zirconium is subsequently deposited on the exposed phosphonate groups for visualization using ToF-SIMS.

Figure 17A:
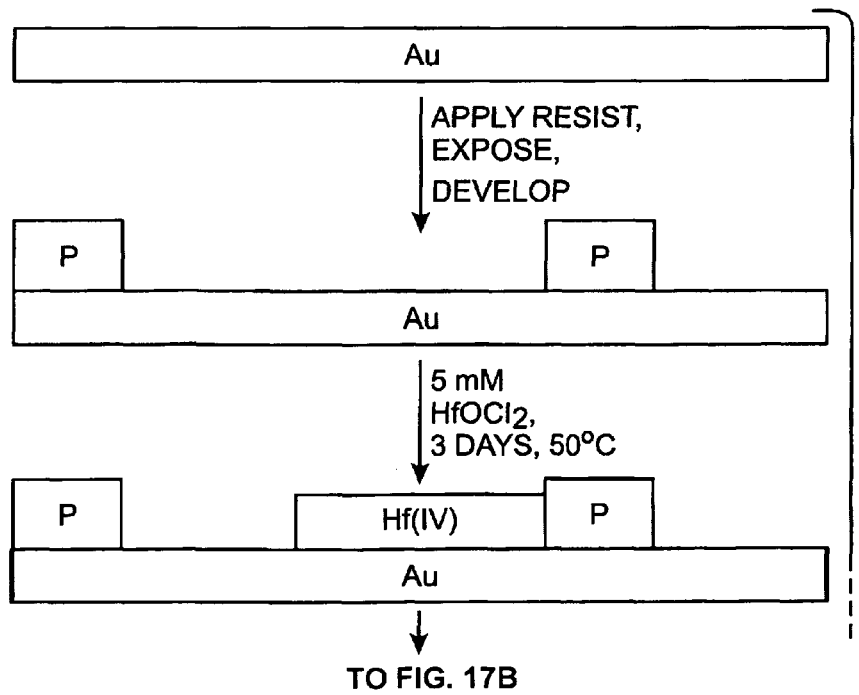
FIGS. 17a-17b illustrate processing steps for fabrication of Hf/Zr patterned substrates.
Figure 17B:
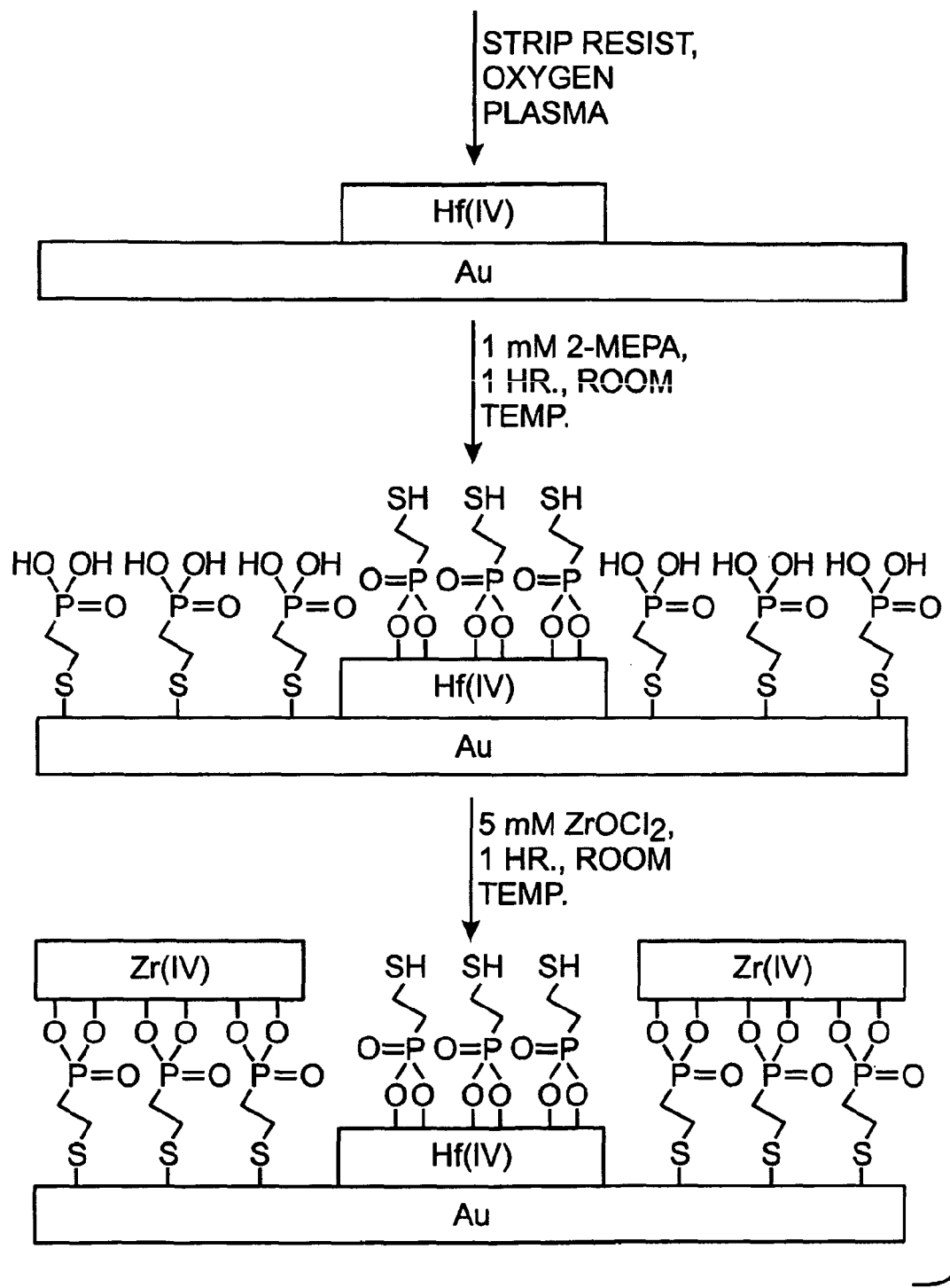
Figure 18A:
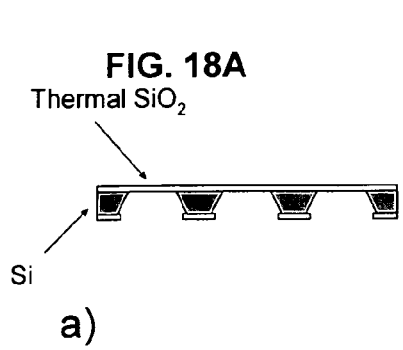
FIGS. 18a-18d illustrate TEM grids for advanced characterization of nanomaterials and devices. Grids are produced using thermal $SiO_2$ grown onto Si wafers (a). The grids can be produced in a wafer format (b) that allows for popping-out the grids for imaging but also enhanced processing and handling. (c) SEM image of 3 mm TEM grid with 12 windows. (d) Underside SEM view of thermal $SiO_2$ windows and etch pit. The $SiO_2$ windows provide for enhanced processing capabilities and control of interfacial chemistry.
Figure 18B:
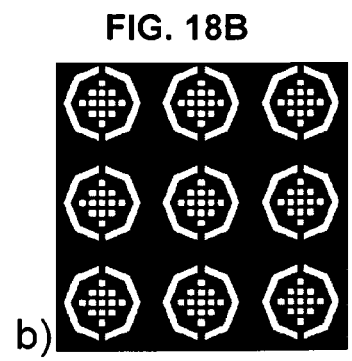
Figure 18C:
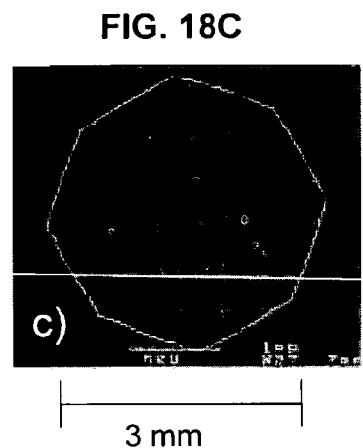
Figure 18D:
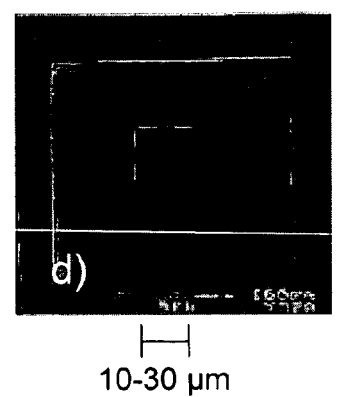

This process embodiment is illustrated in FIGS. 17a-17b. A clean gold film is patterned by photolithography to expose areas of the surface. The patterned film is briefly treated with oxygen plasma to remove any remaining resist from the exposed areas, and the substrate is subsequently soaked in an aqueous solution of $HfOCl_2$. The photoresist is then stripped with acetone, and the substrate is soaked in a solution of 2-MEPA. After rinsing with copious amounts of ethanol the substrate is soaked in an aqueous solution of $ZrOCl_2$ to mark the regions where the phosphonic acid functionality of 2-MEPA is exposed. The final structures were imaged by time-of-flight secondary ion mass spectrometry (ToF-SIMS). ToF-SIMS provide ion yields of the HfO, ZrO, S and $PO_3$ fragments rendering the patterning of hafnium and zirconium clearly visible. The ion yields of $PO_3$ and sulfur also reflect the difference in orientation of 2-MEPA between the hafnium functionalized areas and the bare gold. This example further demonstrates that high quality, stable alkylphosphonate monolayers can be assembled on gold using a hafnium linker molecule, opening up the possibility of functionalizing gold surfaces with a new class of organic monolayers, and demonstrates the production of patterned gold surfaces according to embodiments of the disclosed method.

Functionalized Windows

Silicon grids and representative functionalizations are described above. Additional representative examples are provided based on particular functionalizations that can provide improved nanostructure visualization and characterization in which, for examples, TEM grids are configured to provide a wide range of characterization methods on a single sample. Some applications of such devices include observing the correlation in electronic response and nanoscale structure for single electron transistors, the effects of surface chemistry on adsorption and organization of nanoparticle arrays or atomic arrays onto functionalized surfaces, or the nucleation and self-assembly of 2-D arrays of quantum dots during molecular beam epitaxy and to correlate the structure of these arrays with their performance in quantum computing and quantum cryptography. In other examples, the effects of temperature and deposition parameters on nanostructure evolution can be observed in real-time for advanced coatings, or antibody/antigen interactions can be monitored with antibodies anchored to a functionalized or otherwise sensitized surface. Combining TEM imaging with functionalized substrates permit observation of sub-Angstrom structural features in samples. In disclosed examples, optical, electronic, chemical, and/or biological properties of materials and assemblies can be evaluated in a common sample.

As noted above, thermal $SiO_2$ grid windows can provide grid surfaces on which nanoparticle arrays can be deposited or other surface interactions investigated. The surface chemistry of such grids can be repeatable, and the grids allow structural imaging of the nanoparticle arrays or other interactions. FIGS. 18a-18d show a schematic cross-section of such grids along with scanning electron microscope images of actual grids.

TEM grids such as shown in FIGS. 18a-18d are typically produced via photolithography and wet-chemical etching of thermally oxidized thin Si wafers. Grid and window dimensions and usage form factors can be selected through photolithography and processing conditions. Standard TEM grids are 3 mm octagons with 12 or 16 10-30 µm square windows, but other window shapes can be produces such as slits that are 10-30 µm wide by 2 mm long, with built-in indexing capabilities. Wafers of "pop-out" grids (FIG. 18b) can be provided that conveniently allow enhanced wafer handling and processing for steps such as cleaning, spin coating, and patterning of electrodes. The grids are rigid due to their Si frame and generally do not deform during routine handling.

Window thickness can be controlled by thermal oxidation conditions as well as by post-fabrication etching. Typical grids have windows that are 30-100 nm in thickness. Oxide films are grown at 1100° C. which allows for viscous flow of the oxide to relieve compressive stress introduced during growth. This stress-relief prevents the windows from buckling or breaking when the supporting silicon is etched away. The windows do not appear to be bowed, as there is no evidence of a change in focal plane. While $SiO_2$ glass is known to be a fragile material, particularly at extremely thin dimensions, the geometry of the windows in combination with the oxide growth process results in windows that are surprisingly robust and can withstand multiple processing steps.

The use of thermally-grown $SiO_2$ windows in these grids provides for numerous advantages over other types of TEM grids. First, Si and $SiO_2$ are chemically and thermally stable materials. They are the two most commonly found materials in semiconductor processing and will withstand a wide range of aggressive cleaning procedures including UV/ozone, oxygen plasma treatment, piranha, and RCA cleaning. This allows one to ensure any adsorbed organic or metallic impurities are removed prior to sample preparation. Moreover, it allows one to use acidic solutions for deposition or processing of samples on the grids. The grids can be heated to >1000° C. with little or no change in structure. This temperature stability allows for direct monitoring of changes in structure as a function of temperature for process optimization.

A second advantage is that growth of thermal oxide windows results in ultra-low surface roughness that is imparted by the Si wafer so that the background scattering of these TEM grids is significantly lower than that of conventional grids with thinner windows. Hence, it is possible to use thicker windows for equal or better imaging resolution than other grids to enhance the mechanical properties of the windows.

A third advantage is that thermal $SiO_2$ is representative of one of the most widely functionalized surfaces in analytical chemistry. Unlike other TEM grids, the well-defined surface of thermal $SiO_2$ allows for a wide range of surface modification and chemical functionalization to promote specific and non-specific interaction of the sample with the grid. It is possible to control the relative hydrophobicity and hydrophilicity of the grids by surface modification to enable deposition of a wide range of materials from both aqueous and organic solutions. For example, as-grown carbon nanotubes are hydrophobic which forces them to agglomerate when deposited on hydrophilic surfaces. By modifying the surface of the grids to be hydrophobic, it is possible to preserve their isolated structure for imaging as well as for understanding and possibly optimizing how they deposit on planar surfaces.

In addition to modification of the surface for non-specific interactions, it is possible to modify the surface of the grids to promote the specific interaction and/or covalent attachment of a wide range of chemical and biological molecules to the surface. This allows for observation of interactions with bound species on planar surfaces. As an example, it is possible to covalently attach an antibody to the surface of the grid. This grid could then be immersed in a solution of antigens to observe binding events when the antigen is appropriately labeled.

It is also possible to modify the surface chemistry of the grid from $SiO_2$ to other metal oxides including $TiO_2$, $Al_2O_3$, $ZrO_2$, $Ta_2O_5$ or metal nitrides such as AlN or TiN through atomic layer deposition (ALD) to emulate other materials.

Figure 19:
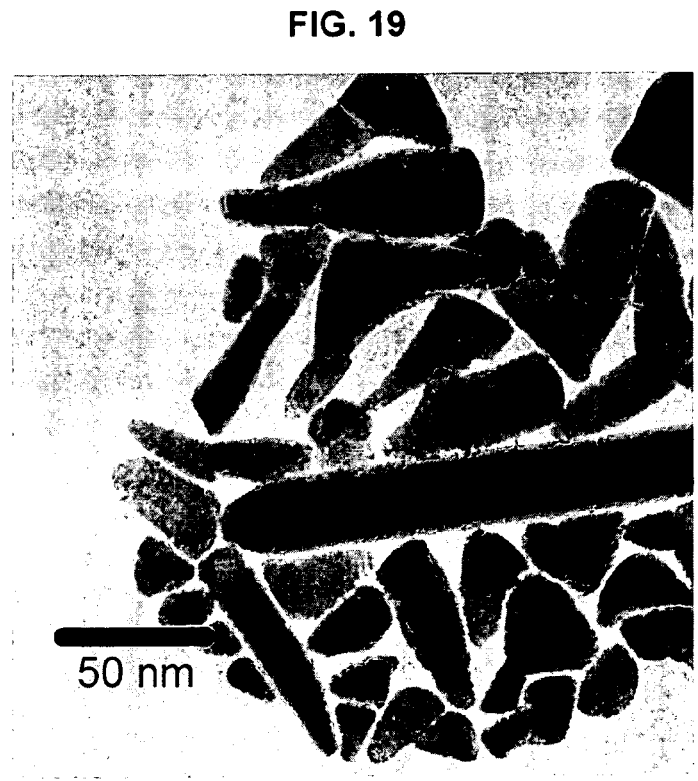
FIG. 19 illustrates zinc oxide nanocrystals deposited onto an $Al_2O_3$-modified $SiO_2$ TEM grid.

These grids can then be used to directly investigate synergistic surface interactions that are observed in catalysis for example. FIG. 19 is an image of commercial ZnO nanopowder (Aldrich) deposited onto an $Al_2O_3$-coated (5 nm) $SiO_2$ grid. The presence of the 5 nm coating of $Al_2O_3$ on the $SiO_2$ grid has been verified by X-ray diffraction and the window shows excellent electron transparency.

These combined features of the $SiO_2$ windows provide for process development in coating technologies in which one could monitor nucleation, growth, and organization of monolayers and multilayers. Conditions favorable for defect formation including dislocations, pinholes, grain boundary effects can be observed. TEM can be used as a part of process optimization for a range of deposition methods including evaporation, atomic layer deposition (ALD), sputtering, spin-on coatings, chemical vapor deposition (CVD), plasma-assisted CVD, and physical vapor deposition (PVD) among others. Step-by step analysis can be used to understand structural evolution in these thin films which serve as seed layers for thicker films. Moreover, one could monitor the effects of surface modification on adhesion of the thin films.

The disclosed TEM grids generally do not exhibit the deficiencies of conventional silicon monoxide ($SiO_x$) and silicon nitride ($Si_3N_4$) based grids. These substrates are not rigid, the surfaces are rough, and $SiO_x$ has an ambiguous chemical structure that is a mixture of SiO and $SiO_{2.6}$. This surface does not have the same well-defined chemical reactivity nor stability as native or thermally grown $SiO_2$ on silicon. Due to the reactivity of the polymer-coated metal grid that typically supports the $SiO_x$ film, these grids cannot withstand even the mildest environments that are used for cleaning and processing $SiO_2$/Si.

Recently, silicon nitride has emerged as a new type of TEM grid that is commercially available from selected vendors. It has been shown that the surfaces of silicon nitride grids can be oxidized through $O_2$ plasma treatment, but the chemical nature and reactivity of the surface has not been determined. It has also been shown that the chemical composition of oxidized silicon nitride surface depends strongly on the method of oxidation, ranging from an oxynitride composition at lower levels of oxidation toward a "silicon oxide-rich" layer after more extensive oxidation. The reactivity of the "native oxide" on silicon nitride has been shown to depend on the method of sample preparation. Given the marked dependence of the surface reactivity of silicon dioxide and oxidized silicon nitride on the method of preparation and given the lack of reliable information regarding the ability to reproducibly functionalize the oxidized $Si_3N_4$ surface, the best approach to reliably image nanostructures on chemically modified surfaces is to use a surface that is prepared in the same manner as will be used for bulk measurements.

Representative Functionalizations

The rich surface chemistry of the $SiO_2$ TEM grids combined with their chemical, thermal and physical stability, creates a unique opportunity to not only improve sample preparation and imaging resolution in TEM, but also to utilize these grids as platforms in a number of advanced applications that will actually accelerate research. As an example, the ability to utilize multiple analytical methods to characterize the samples is unique for these grids and will allow for unprecedented understanding of structure-property relationships. It is possible to combine structural/chemical evaluation of samples deposited on the grids with a wide range of surface analytical techniques including atomic force microscopy (AFM), x-ray photoelectron spectroscopy (XPS), Auger electron spectroscopy (AES), surface-enhanced Raman spectroscopy (SERS), secondary ion mass spectroscopy (SIMS), surface plasmon resonance (SPR), scanning tunneling microscopy (STM), electron energy loss spectroscopy (EELS), scanning electron microscopy (SEM), ellipsometry, and Fourier transform infrared (FTIR) among others.

Figure 20A:
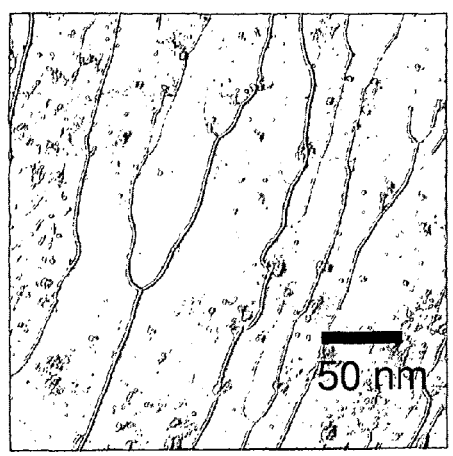
FIGS. 20a-20b illustrate arrays of DNA on TEM grid surfaces. The AFM image of FIG. 20a was recorded using tapping mode AFM in the amplitude setting. The TEM image in FIG. 20b shows Au NPs selective adhesion to branched DNA.
Figure 20B:
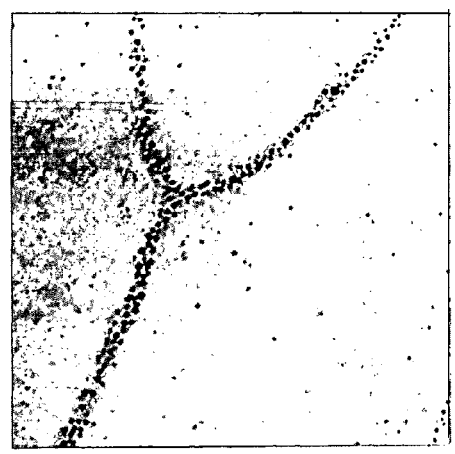

FIGS. 20a-20b show examples of surface analytical techniques applied to 1-D and 2-D arrays of Au nanoparticles deposited on TEM grid surfaces. In both cases, the grids have been carried through multiple processing steps to achieve the desired structure. FIGS. 20a-20b show an AFM image (tapping mode—amplitude) and the corresponding TEM image of an array of DNA stretched across the surface of the TEM grid. The grids were cleaned using RCA SC-1 methods to promote an increased concentration of surface hydroxyl groups. Subsequently, the surface was exposed to octyltrichlorosilane to create a hydrophobic surface. The grid was then soaked in a solution of DNA and pulled from solution to molecularly comb it into a linear array across the surface. The bundling and clumping of the DNA present in FIG. 20b is due to the presence of $MgCl_2$ in the DNA solution. The grid was then soaked in a solution of Au nanoparticles with a positively-charged surface functionality which specifically interacts with the negatively charged phosphate groups in the DNA backbone. These Au particles then provide contrast during imaging for the DNA.

Figure 21A:
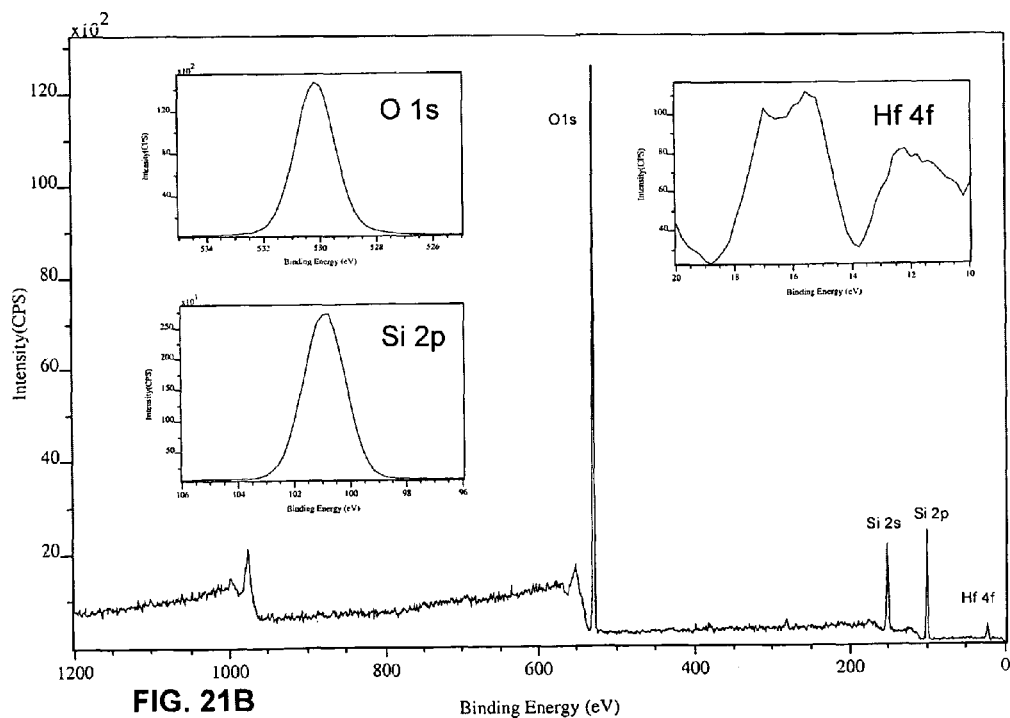
FIG. 21a is an XPS spectrum of an $HfO_2$-functionalized $SiO_2$ TEM grid.
Figure 21B:
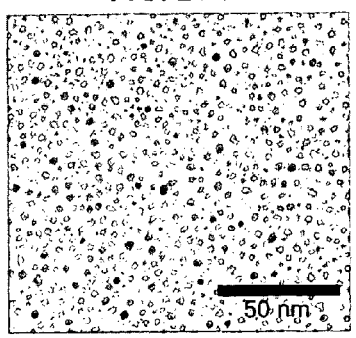
FIG. 21b is a TEM image of an AuNP array assembled on an $HfO_2$ monolayer.

FIG. 21a shows an XPS plot of a TEM grid that has been modified with $HfO_2$ to promote the specific interaction of AuNPs with the grid surface. In this case, the grids were cleaned using oxygen plasma and RCA SC1 treatments followed by functionalization with $HfOCl_2$ to form a monolayer of $HfO_2$. Finally, the grids were soaked in a solution of AuNPs to promote the self-assembly of the phosphonate-functionalized AuNPs on the $HfO_2$ surface. The XPS data in FIG. 21a was taken prior to deposition of the AuNPs to determine the relative coverage of the $HfO_2$ monolayer on the surface of the grid. The O 1s, Si 2p, and Hf 4f peaks are all enlarged in this image. The TEM image of FIG. 21b shows the structure of the 2-D array of AuNPs that have self-assembled onto the grid surface corresponding to the grid of FIG. 21a.

In addition to employing surface analytical methods, it is possible to pattern the grids with electrodes to enable electrical measurements of nanostructures or even single particles including IV curves, impedance spectroscopy, and electrochemical analysis. One can also employ a number of other optical characterization methods including optical microscopy, fluorescence and confocal microscopy, and near-field scanning optical microscopy.

TEM grids with electron transparent $SiO_2$ windows, and chemical functionalizations of the surfaces of such grids can be used in various applications. In addition, grids and functionalizations of non-$SiO_2$ based grids are described below in several additional examples.

Example 1

Surface Modification of Non-$SiO_2$ Electron Transparent Windows

Alternate materials such as $Si_3N_4$ and C can be used for making electron transparent windows and functionalized surfaces can be provided. For example, an $Si_3N_4$ surface can be oxidized using known methods to produce surface silanols. Carbon surfaces can be functionalized using aryl diazonium salts which are known to react with carbon surfaces including carbon nanotubes and highly ordered pyrolitic graphite. In this approach, the diazonium group is reduced, leaving an aryl radical such as a phenyl group, a tolyl group, or an xylyl group which can covalently bond to SP2 hybridized carbon. The aryl group will have substitutions in other positions on the ring which will allow for further chemical modification. These substituents include nitro (—$NO_2$), esters (—COOR), alkanes, polyethylene glycols (—$OC_2H_4$)—, and halogens. The nitro groups can be reduced to amines.

The surface groups installed in this manner can then undergo further chemical modification as described herein. For example, $SiO_2$, $Si_3N_4$ and C surfaces modified by the above procedures can be further processed so as to covalently attach a linker with an amine terminal end, which can then be attached to a biomolecule.

Example 2

Non-Covalent Modifications

Physical deposition of organic moieties such as polymers to achieve desired properties on TEM grid surface can be provided by polymerization in place or spin coating or otherwise produced. Representative polymers include nylon, polyurethane, polysiloxanes and silicone rubber, polyvinylchloride, photoresist, perfluorinated polymers, polyesters, polyalkenes.

Example 3

Covalent Modifications

Surface silanols of $SiO_2$ allow for chemical modification with, for example, hydrophilic or hydrophobic groups, or with bifunctional groups in which one end attaches to surface silanols and the other end presents a functional group that could undergo further reactivity. Other groups that can be attached include PEG chains which are useful for anti-fouling applications, particularly in biological applications to prevent the binding of proteins which would foul the surface of the window. A silane on one end of the molecule can be used as the chemical group to attach to the surface silanols.

Representative hydrophilic groups include alcohol, PEG, MPEG, carboxylate, or other polar groups (e.g. amines, etc.) on the terminal end of a linker (typically aliphatic or aromatic hydrocarbon chains) held to the surface with one of the surface chemistries described above. These are also included in the "bifunctional" description below. Samples with PEG and alcohol groups on $SiO_2$ and $Si_3N_4$ have been produced.

Representative hydrophobic groups include alkyl, perfluoroalkyl or other hydrophobic groups on the terminal end of a linker (typically an aliphatic or aromatic hydrocarbon chain) held to the surface with one of the surface chemistries described above. Samples with alkylsilane coatings have been produced.

Representative bifunctional groups include one end that will attach to the surface silanol (or N in the case of C grids), then a linker, then a functional head group. Representative linkers include hydrocarbons (alkanes, alkenes, alkynes, aromatics). Reactive functional head groups include amines, thiols, carboxylates, alcohols, phosphines, isonitriles, sulfhydryl, phosphonate, hydroxyl. These terminal groups interact to form a link (generally a covalent bond, but also non-covalent bonds such as hydrogen-bonds) with molecules, macromolecules or biomolecules. We have produced samples with amine termination on $SiO_2$, $Si_3N_4$, and C grids.

Representative PEG bifunctional groups include 2-methoxypoly(ethyleneoxy)-propyl trimethoxysilane. The terminal chain consists of a chain of polyethers ranging from a single ethylene glycol unit to polymers of high molecular weight. Typical lengths are 1-5 ethylene glycol units. In addition to homogeneous coatings of the above bifunctional groups, mixtures of bifunctional groups can be used to serve to dilute the reactive groups. A representative example includes mixtures of alkylsilanes with aminoalkylsilanes. Mixed coatings samples have been produced on $SiO_2$ and $Si_3N_4$.

Example 4

Biomolecule Attachment

The use of the surfaces which have been chemically tailored by the covalent attachment of a bifunctional group can be further modified by attachment of a biomolecule via a complementary reactive group. Bifunctional secondary linker molecules are often used which react with the head group of the "covalent chemical groups" described above. These secondary groups allow freedom of movement of the subsequently attached biomolecules described above. Examples include heterobifunctional linkers such as succinimidyl 4-[malemidophenyl] butyrate or 4-(N-maleimidomethyl)cyclohexanecarboxylic acid N-hydroxysuccinimide ester. In these examples, the NHS ester could react with a terminal amine group. The maleimide moiety could react with a sulfhydryl end group on the biomolecule. A list of reactive groups and their target functional group is listed in the table below. The target group can represent either the head group on the surface of the grid or a reactive group on the biomolecule. Representative biomolecules include peptides, proteins, antibodies, antigens, amino acids, and oligosaccharides.

| Reactive Group | Target Functional Group<br>Nonselective (or primary amine) |
|---|---|
| Aryl Azide | Sulfhydryl |
| Maleimide | Sulfhydryl |
| Carbodiimide | Amine/carboxyl |
| NHS-ester | Amine |
| Hydrazide | Carbohydrate (oxidized) |
| PFP-ester | Amine |
| Hydroxymethyl | |
| Phosphine | Amine |
| Psoralen | Thymine (photoreactive intercalator) |
| Imidoester | Amine |
| Pyridyl Disulfide | Sulfhydryl |
| Isocyanate | Hydroxyl (non-aqueous) |
| Vinyl Sulfone | Sulfhydryl, amine, hydroxyl |
| Carbonyl | Hydrazine |

Example 5

Inorganic Surface Modifications

The surfaces of the electron-transparent windows can also be modified by coating with various inorganic materials such as metal oxides or ceramics to create a selected chemical surface. Such chemically prepared surfaces can permit direct imaging of samples deposited on surfaces that are substantial the same as real-world materials. These inorganic materials can be deposited by ALD (atomic layer deposition), CVD (chemical vapor deposition), spin-on procedures, or other deposition methods. Representative inorganic materials include: $TiO_2$, tricalcium phosphate, hyrdoxyapatite, indium tin oxide (a conductive metal oxide), $HfO_2$ and $ZrO_2$, aluminum oxide, tin oxide, iron oxide, zinc oxide, etc. Coatings of at least $TiO_2$, $Al_2O_3$, $HfO_2$, $ZrO_2$ have been produced.

Example 6

Modifications or Applications of Physical Properties

The "underside" of a grid as a series of small-volume wells formed on or by a TEM grid can also be used. For example, such wells can be used to contain samples produced by focused ion beam (FIB) milling. FIB is a method that is routinely used to "cut" thin specimens, or lamellae, from larger samples that are then examined using TEM. The thin specimen must be carefully removed from the bulk sample and placed on a TEM grid for analysis. This method is widely used in the semiconductor industry as a quality control tool for wafers. Currently, the samples are either placed on top of the grid or are "welded" in placed using an electron beam. There is a problem with the samples sliding off the surface or at least moving around. The wells of the $SiO_2$ grids can contain the grids without the need for welding and can provide indexing capability since one knows which well each sample was placed in.

The "bottom" side of the window (inside the well) can be used to hold deposited nanoparticles and nanomaterials with known sizes/shapes that can serve as calibration standards for samples deposited on top of the grids. As an example, gold nanoparticles with size in the range 1-20 nm and narrow size distribution could be deposited on the bottom side of the window. The gold can be imaged separately from the sample on top to calibrate the TEM since it is in a different focal plan. The gold would not interfere with the sample on top of the grid since there is no communication between the two sides.

As described above, "hydrated" $SiO_2$/Si windows can be provided wherein the native $SiO_2$ is hydrated with surface silanols. Silanating agents with hydrophobic or hydrophilic tails can be provided to form hydrophilic or hydrophobic $SiO_2$. $SiO_2$ surface can be treated so as to form $SiO_2$—X-L-Y, wherein X is a group that covalently or otherwise modifies the $SiO_2$ surface, L is a linking molecule such as a hydrocarbon, and Y is a functional group (such as amines, ammoniums, carboxylic acids, thiols, phosphonates). Inorganic $SiO_2$ modifications can be provided using Hf(IV) and a linker in a solution based approach, or atomic layer deposition (ALD) can be used (examples include $Al_2O_3$, $HfO_2$, $ZrO_2$ or other surfaces that can be provided by ALD).

Grids can be formed in a lacey/holey configuration in which $SiO_2$ windows include a regular or irregular pattern of holes or a single hole. Etch processes or electron beam or ion beam milling can be used. Windows can be thinned by dry etching to reduce background without exposure to solution processing. A backside of a window can be etched so that surface modifications on an opposing surface remain undisturbed. Electrodes can be built in or onto the $SiO_2$ window surface. Self-assembly of nanoparticles onto these electrodes allows direct device imaging.

In view of the many possible embodiments to which the principles of the disclosed technology may be applied, it should be recognized that the illustrated embodiments are only representative examples, and we claim all that is encompassed by the appended claims.

We claim:

1. A substrate, comprising:
a silicon layer in which an electron-transmissive aperture is defined; and
an electron transmissive oxide layer situated in the aperture.

2. The substrate of claim 1, wherein the oxide layer comprises a metallic oxide.

3. The substrate of claim 2, wherein the oxide layer comprises an oxide of at least one of hafnium, aluminum, tin, iron, zinc, and zirconium.

4. The substrate of claim 2, wherein the oxide layer comprises indium tin oxide.

5. The substrate of claim 1, wherein an exterior surface of the oxide layer is functionalized.

6. A substrate, comprising:
a silicon layer;
an electron-transmissive aperture layer defined in the silicon layer, wherein the electron-transmissive layer comprises at least one of $Si_3N_4$ and $SiO_2$ and includes at least one functionalized surface.

7. The substrate of claim 6, wherein the functionalized surface comprises silanols.

8. The substrate of claim 6, wherein the functionalized surface comprises aryl groups.

9. The substrate of claim 8, wherein the functionalized surface comprises aryl groups that include substituents selected from the group comprising nitro groups, esters alkanes, polyethylene glycols, and halogens.

10. The substrate of claim 8, wherein the functionalized surface comprises amines.

11. The substrate of claim 6, wherein the electron-transmissive layer comprises $Si_3N_4$, and the functionalized surface comprises silanols.

12. A substrate, comprising:
a silicon layer in which an electron-transmissive aperture is defined; and
an electron transmissive polymer layer situated in the aperture.

13. The substrate of claim 12, wherein the electron transmissive polymer layer comprises at least one of a polyvinylchloride, a photoresist, a perfluorinated polymer, a polyester, and a polyalkene.

14. The substrate of claim 13, wherein the aperture is an etched portion of the substrate.

15. A substrate, comprising:
a silicon-containing layer in which an electron-transmissive aperture layer is defined, wherein the aperture layer includes a functionalized surface comprising a hydrophilic group moiety, a hydrophobic group moiety, or a bifunctional group moiety.

16. The substrate of claim 15, wherein the functionalized surface comprises a hydrophilic group moiety selected from a group comprising alcohols, polyethylene glycols, methoxypoly(ethylene glycol)), carboxylates, and amines.

17. The substrate of claim 16, wherein the hydrophilic group moiety is secured to the substrate by a linker group.

18. The substrate of claim 17, wherein the linker is an aliphatic or aromatic hydrocarbon chain.

19. The substrate of claim 15, wherein the silicon-containing substrate is $SiO_2$ Or $Si_3N_4$.

20. The substrate of claim 15, wherein the functionalized surface comprises an alkyl hydrophobic group moiety.

21. The substrate of claim 15, wherein the functionalized surface comprises at least one bifunctional moiety selected to attach to the aperture layer and a linker moiety.

22. The substrate of claim 21, wherein the linker moiety is an alkane, alkene, alkyne, or an aromatic moiety.

23. The substrate of claim 22, wherein the linker moiety includes a reactive functional head group selected from the group comprising amines, thiols, carboxylates, alcohols, phosphines, isonitriles, sulfhydryls, phosphonates, and hydroxyls.

24. The substrate of claim 21, wherein the bifunctional moiety is a polyethylene glycol.

25. The substrate of claim 24, wherein the polyethylene glycol comprises fewer than ten ethylene glycol units.

26. A method, comprising:
providing an electron-transmissive window in a substrate; and
contacting a surface of the electron-transmissive window so as to functionalize the surface.

27. The method of claim 26, wherein the contacting comprises depositing a layer of a polymer or a metal oxide on the surface of the electron-transmissive window.

28. The method of claim 26, wherein the contacting comprises exposing the surface of the electron-transmissive window to a hydrophobic, hydrophilic, or bifunctional moiety.

29. The method of claim 26, wherein the electron-transmissive window is provided by forming a window layer on at least one surface of a substrate, exposing the substrate to an etchant to form at least one aperture, wherein an etch rate of the substrate as exposed to the etchant is substantially larger than an etch rate of the window layer as exposed to the etchant.

30. The method of claim 26, wherein the surface is functionalized by applying a coating by atomic layer deposition, chemical vapor deposition, or as a spin coating.

31. The method of claim 26, wherein the contacting comprises exposing the surface to a moiety selected from the group comprising sulfhydryls, amines, hydroxyls, carbonyls, carboxyls, aryl azide, maleimide, carbodiimide, hydrazine, psoralen, and imidoester.

* * * * *